US011918542B2

(12) United States Patent
Yedgar et al.

(10) Patent No.: US 11,918,542 B2
(45) Date of Patent: Mar. 5, 2024

(54) LIQUID TRANSFER DEVICE

(71) Applicant: West Pharma. Services IL, Ltd., Ra'anana (IL)

(72) Inventors: Aviad Yedgar, Tel Aviv (IL); Amir Lev, Kfar Saba (IL); Uri David, Nes Ziona (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 430 days.

(21) Appl. No.: 17/427,155

(22) PCT Filed: Jan. 31, 2020

(86) PCT No.: PCT/IB2020/050790
§ 371 (c)(1),
(2) Date: Jul. 30, 2021

(87) PCT Pub. No.: WO2020/157719
PCT Pub. Date: Aug. 6, 2020

(65) Prior Publication Data
US 2022/0125680 A1    Apr. 28, 2022

Related U.S. Application Data

(60) Provisional application No. 62/799,317, filed on Jan. 31, 2019.

(51) Int. Cl.
*A61J 1/20* (2006.01)
*A61M 39/10* (2006.01)
(52) U.S. Cl.
CPC ........... *A61J 1/2058* (2015.05); *A61J 1/2089* (2013.01); *A61J 1/2096* (2013.01); *A61M 39/1011* (2013.01)

(58) Field of Classification Search
CPC ................. A61J 1/2058; A61M 39/10111
See application file for complete search history.

(56) References Cited

U.S. PATENT DOCUMENTS

| 62,333   | A | 2/1867  | Hall         |
| 247,975  | A | 10/1881 | Wickes       |
| 254,444  | A | 2/1882  | Vogel et al. |

(Continued)

FOREIGN PATENT DOCUMENTS

| CA | 2946559 A1 | 10/2015 |
| CN | 1636605 A  | 7/2005  |

(Continued)

OTHER PUBLICATIONS

U.S. Appl. No. 14/504,979 by Lev, filed Oct. 2, 2014.

(Continued)

*Primary Examiner* — Leslie R Deak
(74) *Attorney, Agent, or Firm* — Blank Rome LLP

(57) ABSTRACT

A liquid transfer device is described. The device comprises a connector body comprising a projection portion defining a tab and an IV port arranged at a first end of the connector body, the IV port comprising an elongate connecting member projecting therefrom and defining a cutout. The projection portion is configured to be received by the elongate connecting member, and the tab is configured to mate with the cutout so as to rotationally fix the IV port relative to the connector body.

20 Claims, 8 Drawing Sheets

(56) References Cited

U.S. PATENT DOCUMENTS

| | | |
|---|---|---|
| 300,060 A | 6/1884 | Ford |
| 1,021,681 A | 3/1912 | Jennings |
| 1,704,817 A | 3/1929 | Ayers |
| 1,930,944 A | 10/1933 | Schmitz, Jr. |
| 2,326,490 A | 8/1943 | Perelson |
| 2,560,162 A | 7/1951 | Ferguson |
| 2,748,769 A | 6/1956 | Jennie |
| 2,830,587 A | 4/1958 | James |
| 2,931,668 A | 4/1960 | Baley |
| 2,968,497 A | 1/1961 | Mervyn |
| 3,059,643 A | 10/1962 | Barton |
| D198,499 S | 6/1964 | Andrew et al. |
| 3,225,763 A | 12/1965 | Waterman |
| 3,277,893 A | 10/1966 | Clark |
| 3,308,822 A | 3/1967 | De Luca |
| 3,484,849 A | 12/1969 | Huebner et al. |
| 3,618,637 A | 11/1971 | Santomier |
| 3,757,981 A | 9/1973 | Harris, Sr. et al. |
| D229,518 S | 12/1973 | Bujan |
| 3,782,365 A | 1/1974 | Pinna |
| 3,788,524 A | 1/1974 | Davis et al. |
| 3,822,700 A | 7/1974 | Pennington |
| 3,826,261 A | 7/1974 | Killinger |
| 3,872,992 A | 3/1975 | Larson |
| 3,885,607 A | 5/1975 | Peltier |
| 3,938,520 A | 2/1976 | Scislowicz et al. |
| 3,957,052 A | 5/1976 | Topham |
| 3,977,555 A | 8/1976 | Larson |
| 3,993,063 A | 11/1976 | Larrabee |
| 4,020,839 A | 5/1977 | Klapp |
| 4,026,128 A | 5/1977 | Blanco |
| 4,051,852 A | 10/1977 | Villari |
| D247,975 S | 5/1978 | Luther |
| D248,568 S | 7/1978 | Ismach |
| 4,109,670 A | 8/1978 | Slagel |
| 4,121,585 A | 10/1978 | Becker, Jr. |
| 4,161,178 A | 7/1979 | Genese |
| 4,187,848 A | 2/1980 | Taylor |
| D254,444 S | 3/1980 | Levine |
| 4,203,067 A | 5/1980 | Bollongino et al. |
| 4,203,443 A | 5/1980 | Genese |
| 4,210,173 A | 7/1980 | Choksi et al. |
| D257,286 S | 10/1980 | Folkman |
| 4,253,501 A | 3/1981 | Ogle |
| 4,262,671 A | 4/1981 | Kersten |
| 4,296,786 A | 10/1981 | Brignola |
| 4,303,067 A | 12/1981 | Connolly et al. |
| 4,312,349 A | 1/1982 | Cohen |
| 4,314,586 A | 2/1982 | Folkman |
| 4,328,802 A | 5/1982 | Curley et al. |
| 4,335,717 A | 6/1982 | Bujan et al. |
| D267,199 S | 12/1982 | Koenig |
| 4,364,387 A | 12/1982 | Larkin |
| 4,376,634 A | 3/1983 | Prior et al. |
| D268,871 S | 5/1983 | Benham et al. |
| 4,392,850 A | 7/1983 | Elias et al. |
| D270,282 S | 8/1983 | Gross |
| 4,410,321 A | 10/1983 | Pearson et al. |
| 4,411,662 A | 10/1983 | Pearson |
| D271,421 S | 11/1983 | Fetterman |
| 4,434,823 A | 3/1984 | Hudspith |
| 4,465,471 A | 8/1984 | Harris et al. |
| 4,475,915 A | 10/1984 | Sloane |
| 4,493,348 A | 1/1985 | Lemmons |
| 4,505,709 A | 3/1985 | Froning et al. |
| 4,507,113 A | 3/1985 | Dunlap |
| D280,018 S | 8/1985 | Scott |
| 4,532,969 A | 8/1985 | Kwaan |
| 4,534,758 A | 8/1985 | Akers et al. |
| 4,561,445 A | 12/1985 | Berke et al. |
| 4,564,054 A | 1/1986 | Gustavsson |
| 4,573,993 A | 3/1986 | Hoag et al. |
| 4,576,211 A | 3/1986 | Valentini et al. |
| 4,581,014 A | 4/1986 | Millerd et al. |
| 4,585,446 A | 4/1986 | Kempf |
| 4,588,396 A | 5/1986 | Stroebel et al. |
| 4,588,403 A | 5/1986 | Weiss et al. |
| D284,603 S | 7/1986 | Loignon |
| 4,604,093 A | 8/1986 | Brown et al. |
| 4,607,671 A | 8/1986 | Aalto et al. |
| 4,614,437 A | 9/1986 | Buehler |
| 4,638,975 A | 1/1987 | Iuchi et al. |
| 4,639,019 A | 1/1987 | Mittleman |
| 4,667,927 A | 5/1987 | Oscarsson |
| 4,675,020 A | 6/1987 | Mcphee |
| 4,676,530 A | 6/1987 | Nordgren et al. |
| D291,490 S | 8/1987 | Raines |
| 4,683,975 A | 8/1987 | Booth et al. |
| 4,697,622 A | 10/1987 | Swift et al. |
| 4,721,133 A | 1/1988 | Sundblom |
| 4,729,401 A | 3/1988 | Raines |
| 4,735,608 A | 4/1988 | Sardam |
| 4,743,229 A | 5/1988 | Chu |
| 4,743,243 A | 5/1988 | Vaillancourt |
| 4,752,292 A | 6/1988 | Lopez et al. |
| 4,758,235 A | 7/1988 | Tu |
| 4,759,756 A | 7/1988 | Forman et al. |
| 4,778,447 A | 10/1988 | Velde et al. |
| 4,787,898 A | 11/1988 | Raines |
| 4,797,898 A | 1/1989 | Martinez |
| D300,060 S | 2/1989 | Molgaard-Nielsen |
| 4,804,366 A | 2/1989 | Zdeb et al. |
| 4,826,492 A | 5/1989 | Magasi |
| 4,832,690 A | 5/1989 | Kuu |
| 4,834,152 A | 5/1989 | Howson et al. |
| 4,834,744 A | 5/1989 | Ritson |
| D303,013 S | 8/1989 | Konopka |
| 4,857,062 A | 8/1989 | Russell |
| 4,865,592 A | 9/1989 | Rycroft |
| 4,871,463 A | 10/1989 | Taylor et al. |
| 4,898,209 A | 2/1990 | Zdeb |
| 4,909,290 A | 3/1990 | Coccia |
| 4,919,596 A | 4/1990 | Slate et al. |
| 4,927,423 A | 5/1990 | Malmborg |
| 4,931,040 A | 6/1990 | Haber et al. |
| 4,932,944 A | 6/1990 | Jagger et al. |
| 4,967,797 A | 11/1990 | Manska |
| D314,050 S | 1/1991 | Sone |
| D314,622 S | 2/1991 | Andersson et al. |
| 4,997,430 A | 3/1991 | Van Der Heiden et al. |
| 5,006,114 A | 4/1991 | Rogers et al. |
| 5,035,686 A | 7/1991 | Crittenden et al. |
| 5,041,105 A | 8/1991 | D'Alo et al. |
| 5,045,066 A | 9/1991 | Scheuble et al. |
| 5,049,129 A | 9/1991 | Zdeb et al. |
| 5,053,015 A | 10/1991 | Gross |
| 5,061,248 A | 10/1991 | Sacco |
| 5,088,996 A | 2/1992 | Kopfer et al. |
| 5,096,575 A | 3/1992 | Cosack |
| 5,104,387 A | 4/1992 | Pokorney et al. |
| 5,113,904 A | 5/1992 | Aslanian |
| 5,122,124 A | 6/1992 | Novacek et al. |
| 5,125,908 A | 6/1992 | Cohen |
| 5,125,915 A | 6/1992 | Berry et al. |
| D328,788 S | 8/1992 | Sagae et al. |
| D331,281 S | 11/1992 | Levine |
| 5,171,230 A | 12/1992 | Eland et al. |
| 5,181,508 A | 1/1993 | Poole, Jr. |
| 5,201,705 A | 4/1993 | Berglund et al. |
| 5,201,717 A | 4/1993 | Wyatt et al. |
| 5,203,771 A | 4/1993 | Melker et al. |
| 5,203,775 A | 4/1993 | Frank et al. |
| 5,211,638 A | 5/1993 | Dudar et al. |
| D337,828 S | 7/1993 | David |
| 5,232,029 A | 8/1993 | Knox et al. |
| 5,232,109 A | 8/1993 | Tirrell et al. |
| 5,242,432 A | 9/1993 | Defrank |
| 5,247,972 A | 9/1993 | Tetreault |
| D341,420 S | 11/1993 | Conn |
| 5,269,768 A | 12/1993 | Cheung |
| 5,270,219 A | 12/1993 | Decastro et al. |
| 5,279,576 A | 1/1994 | Loo et al. |
| 5,288,290 A | 2/1994 | Brody |
| 5,300,034 A | 4/1994 | Behnke et al. |

(56) References Cited

U.S. PATENT DOCUMENTS

| | | |
|---|---|---|
| 5,301,685 A | 4/1994 | Guirguis |
| 5,304,163 A | 4/1994 | Bonnici et al. |
| 5,304,165 A | 4/1994 | Haber et al. |
| 5,308,483 A | 5/1994 | Sklar et al. |
| 5,312,377 A | 5/1994 | Dalton |
| 5,328,474 A | 7/1994 | Raines |
| D349,648 S | 8/1994 | Tirrell et al. |
| 5,334,163 A | 8/1994 | Sinnett |
| 5,334,179 A | 8/1994 | Poli et al. |
| 5,342,346 A | 8/1994 | Honda et al. |
| 5,344,417 A | 9/1994 | Wadsworth, Jr. |
| 5,348,544 A | 9/1994 | Sweeney et al. |
| 5,348,548 A | 9/1994 | Meyer et al. |
| 5,350,372 A | 9/1994 | Ikeda et al. |
| 5,364,386 A | 11/1994 | Fukuoka et al. |
| 5,364,387 A | 11/1994 | Sweeney |
| 5,374,264 A | 12/1994 | Wadsworth, Jr. |
| 5,385,547 A | 1/1995 | Wong et al. |
| 5,397,303 A | 3/1995 | Sancoff et al. |
| D357,733 S | 4/1995 | Matkovich |
| 5,429,614 A | 7/1995 | Fowles et al. |
| 5,433,330 A | 7/1995 | Yatsko et al. |
| 5,445,630 A | 8/1995 | Richmond |
| 5,445,631 A | 8/1995 | Uchida |
| D362,718 S | 9/1995 | Deily et al. |
| 5,451,374 A | 9/1995 | Molina |
| 5,454,805 A | 10/1995 | Brony |
| 5,464,111 A | 11/1995 | Vacek et al. |
| 5,464,123 A | 11/1995 | Scarrow |
| 5,466,219 A | 11/1995 | Lynn et al. |
| 5,466,220 A | 11/1995 | Brenneman |
| 5,470,327 A | 11/1995 | Helgren et al. |
| 5,471,994 A | 12/1995 | Guirguis |
| 5,472,022 A | 12/1995 | Michel et al. |
| 5,478,337 A | 12/1995 | Okamoto et al. |
| 5,482,446 A | 1/1996 | Williamson et al. |
| 5,492,147 A | 2/1996 | Challender et al. |
| 5,496,274 A | 3/1996 | Graves et al. |
| D369,406 S | 4/1996 | Niedospial et al. |
| 5,505,714 A | 4/1996 | Dassa et al. |
| 5,509,433 A | 4/1996 | Paradis |
| 5,515,871 A | 5/1996 | Bittner et al. |
| 5,520,659 A | 5/1996 | Hedges |
| 5,526,853 A | 6/1996 | Mcphee et al. |
| 5,527,306 A | 6/1996 | Raining |
| 5,531,695 A | 7/1996 | Swisher |
| 5,547,471 A | 8/1996 | Thompson et al. |
| 5,549,577 A | 8/1996 | Siegel et al. |
| 5,554,128 A | 9/1996 | Hedges |
| 5,562,686 A | 10/1996 | Sauer et al. |
| 5,562,696 A | 10/1996 | Nobles et al. |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley et al. |
| 5,603,706 A | 2/1997 | Wyatt et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,637,101 A | 6/1997 | Shillington |
| 5,641,010 A | 6/1997 | Maier |
| 5,645,538 A | 7/1997 | Richmond |
| 5,647,845 A | 7/1997 | Haber et al. |
| 5,651,776 A | 7/1997 | Appling et al. |
| 5,653,686 A | 8/1997 | Coulter et al. |
| 5,658,133 A | 8/1997 | Anderson et al. |
| 5,672,160 A | 9/1997 | Oesterlind et al. |
| 5,674,195 A | 10/1997 | Truthan |
| 5,676,346 A | 10/1997 | Leinsing |
| 5,685,845 A | 11/1997 | Grimard |
| D388,172 S | 12/1997 | Cipes |
| 5,699,821 A | 12/1997 | Paradis |
| 5,702,019 A | 12/1997 | Grimard |
| 5,718,346 A | 2/1998 | Weiler |
| 5,728,087 A | 3/1998 | Niedospial, Jr. |
| D393,722 S | 4/1998 | Fangrow et al. |
| 5,738,144 A | 4/1998 | Rogers |
| 5,743,312 A | 4/1998 | Pfeifer et al. |
| 5,746,733 A | 5/1998 | Capaccio et al. |
| 5,752,942 A | 5/1998 | Doyle et al. |
| 5,755,696 A | 5/1998 | Caizza |
| 5,766,211 A | 6/1998 | Wood et al. |
| 5,772,630 A | 6/1998 | Ljungquist |
| 5,772,652 A | 6/1998 | Zielinski |
| RE35,841 E | 7/1998 | Frank et al. |
| 5,776,116 A | 7/1998 | Lopez et al. |
| 5,782,872 A | 7/1998 | Mueller |
| 5,806,831 A | 9/1998 | Paradis |
| 5,810,792 A | 9/1998 | Fangrow et al. |
| 5,814,020 A | 9/1998 | Gross |
| D399,558 S | 10/1998 | Guala et al. |
| D399,559 S | 10/1998 | Molina |
| 5,817,082 A | 10/1998 | Niedospial et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,834,744 A | 11/1998 | Risman |
| 5,839,715 A | 11/1998 | Leinsing |
| D403,398 S | 12/1998 | Guala et al. |
| 5,853,406 A | 12/1998 | Masuda et al. |
| D405,522 S | 2/1999 | Hoenig et al. |
| 5,868,710 A | 2/1999 | Battiato et al. |
| 5,871,110 A | 2/1999 | Grimard et al. |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,890,610 A | 4/1999 | Jansen et al. |
| 5,891,129 A | 4/1999 | Daubert et al. |
| 5,893,397 A | 4/1999 | Peterson et al. |
| 5,897,526 A | 4/1999 | Vaillancourt |
| 5,899,468 A | 5/1999 | Apps et al. |
| 5,902,280 A | 5/1999 | Powles et al. |
| 5,902,298 A | 5/1999 | Niedospial et al. |
| D410,740 S | 6/1999 | Molina |
| 5,911,710 A | 6/1999 | Barry et al. |
| 5,919,182 A | 7/1999 | Avallone |
| 5,921,419 A | 7/1999 | Niedospial et al. |
| 5,924,584 A | 7/1999 | Hellstrom et al. |
| 5,925,029 A | 7/1999 | Jansen et al. |
| 5,935,112 A | 8/1999 | Stevens et al. |
| 5,941,848 A | 8/1999 | Nishimoto et al. |
| 5,941,850 A | 8/1999 | Shah et al. |
| 5,944,700 A | 8/1999 | Nguyen et al. |
| D414,562 S | 9/1999 | Tajima |
| 5,954,104 A | 9/1999 | Daubert et al. |
| 5,968,022 A | 10/1999 | Saito |
| 5,971,181 A | 10/1999 | Niedospial et al. |
| 5,971,965 A | 10/1999 | Mayer |
| D416,086 S | 11/1999 | Parris et al. |
| 5,989,237 A | 11/1999 | Fowles et al. |
| D417,733 S | 12/1999 | Howell et al. |
| 6,003,566 A | 12/1999 | Thibault et al. |
| 6,004,278 A | 12/1999 | Botich et al. |
| 6,019,750 A | 2/2000 | Fowles et al. |
| 6,022,339 A | 2/2000 | Fowles et al. |
| 6,036,171 A | 3/2000 | Weinheimer et al. |
| 6,039,093 A | 3/2000 | Mrotzek et al. |
| 6,039,302 A | 3/2000 | Cote et al. |
| D422,357 S | 4/2000 | Niedospial et al. |
| 6,053,899 A | 4/2000 | Slanda et al. |
| 6,063,068 A | 5/2000 | Fowles et al. |
| D427,308 S | 6/2000 | Zinger |
| D427,309 S | 6/2000 | Molina |
| 6,070,623 A | 6/2000 | Aneas |
| 6,071,270 A | 6/2000 | Fowles et al. |
| 6,080,132 A | 6/2000 | Cole et al. |
| D428,141 S | 7/2000 | Brotspies et al. |
| 6,086,762 A | 7/2000 | Guala |

(56) References Cited

U.S. PATENT DOCUMENTS

| | | |
|---|---|---|
| 6,089,541 A | 7/2000 | Weinheimer et al. |
| 6,090,091 A | 7/2000 | Fowles et al. |
| 6,090,093 A | 7/2000 | Thibault et al. |
| 6,092,692 A | 7/2000 | Riskin |
| D430,291 S | 8/2000 | Jansen et al. |
| 6,099,511 A | 8/2000 | Devos et al. |
| 6,113,068 A | 9/2000 | Ryan |
| 6,113,583 A | 9/2000 | Fowles et al. |
| 6,117,114 A | 9/2000 | Paradis |
| D431,864 S | 10/2000 | Jansen |
| 6,139,534 A | 10/2000 | Niedospial et al. |
| 6,142,446 A | 11/2000 | Leinsing |
| 6,146,362 A | 11/2000 | Turnbull et al. |
| 6,149,623 A | 11/2000 | Reynolds |
| 6,156,025 A | 12/2000 | Niedospial et al. |
| 6,159,192 A | 12/2000 | Fowles et al. |
| 6,162,199 A | 12/2000 | Geringer |
| 6,168,037 B1 | 1/2001 | Grimard |
| 6,171,287 B1 | 1/2001 | Lynn et al. |
| 6,171,293 B1 | 1/2001 | Rowley et al. |
| 6,173,852 B1 | 1/2001 | Browne |
| 6,173,868 B1 | 1/2001 | Dejonge |
| 6,174,304 B1 | 1/2001 | Weston |
| 6,179,822 B1 | 1/2001 | Niedospial, Jr. |
| 6,179,823 B1 | 1/2001 | Niedospial, Jr. |
| 6,186,997 B1 | 2/2001 | Gabbard et al. |
| 6,206,861 B1 | 3/2001 | Mayer |
| 6,221,041 B1 | 4/2001 | Russo |
| 6,221,054 B1 | 4/2001 | Martin et al. |
| 6,221,065 B1 | 4/2001 | Davis |
| 6,238,372 B1 | 5/2001 | Zinger et al. |
| 6,245,044 B1 | 6/2001 | Daw et al. |
| D445,501 S | 7/2001 | Niedospial |
| D445,895 S | 7/2001 | Svendsen |
| 6,253,804 B1 | 7/2001 | Safabash |
| 6,258,078 B1 | 7/2001 | Thilly |
| 6,280,430 B1 | 8/2001 | Neftel et al. |
| 6,290,688 B1 | 9/2001 | Lopez et al. |
| 6,296,621 B1 | 10/2001 | Masuda et al. |
| 6,299,131 B1 | 10/2001 | Ryan |
| D453,221 S | 1/2002 | Haytman et al. |
| 6,343,629 B1 | 2/2002 | Wessman et al. |
| 6,348,044 B1 | 2/2002 | Coletti et al. |
| 6,358,236 B1 | 3/2002 | Defoggi et al. |
| 6,364,866 B1 | 4/2002 | Furr et al. |
| 6,378,576 B2 | 4/2002 | Thibault et al. |
| 6,378,714 B1 | 4/2002 | Jansen et al. |
| 6,379,340 B1 | 4/2002 | Zinger et al. |
| D457,954 S | 5/2002 | Wallace et al. |
| 6,382,442 B1 | 5/2002 | Thibault et al. |
| 6,386,397 B2 | 5/2002 | Brotspies et al. |
| 6,408,897 B1 | 6/2002 | Laurent et al. |
| 6,409,708 B1 | 6/2002 | Wessman |
| 6,419,696 B1 | 7/2002 | Ortiz et al. |
| 6,440,107 B1 | 8/2002 | Trombley et al. |
| 6,453,949 B1 | 9/2002 | Chau |
| 6,453,956 B2 | 9/2002 | Safabash |
| 6,474,375 B2 | 11/2002 | Spero et al. |
| 6,478,788 B1 | 11/2002 | Aneas |
| D468,015 S | 12/2002 | Horppu |
| 6,499,617 B1 | 12/2002 | Niedospial et al. |
| 6,503,240 B1 | 1/2003 | Niedospial et al. |
| 6,503,244 B2 | 1/2003 | Hayman |
| 6,520,932 B2 | 2/2003 | Taylor |
| 6,524,278 B1 | 2/2003 | Campbell et al. |
| 6,524,295 B2 | 2/2003 | Daubert et al. |
| D472,316 S | 3/2003 | Douglas et al. |
| 6,530,903 B2 | 3/2003 | Wang et al. |
| 6,537,263 B1 | 3/2003 | Aneas |
| D472,630 S | 4/2003 | Douglas et al. |
| 6,544,246 B1 | 4/2003 | Niedospial |
| 6,551,299 B2 | 4/2003 | Miyoshi et al. |
| 6,558,365 B2 | 5/2003 | Zinger et al. |
| 6,569,196 B1 | 5/2003 | Vesely |
| 6,571,837 B2 | 6/2003 | Jansen et al. |
| 6,572,591 B2 | 6/2003 | Mayer |
| 6,575,955 B2 | 6/2003 | Azzolini |
| 6,581,593 B1 | 6/2003 | Rubin et al. |
| 6,581,648 B1 | 6/2003 | Zolentroff et al. |
| 6,582,415 B1 | 6/2003 | Fowles et al. |
| D476,731 S | 7/2003 | Cise et al. |
| 6,591,876 B2 | 7/2003 | Safabash |
| 6,599,273 B1 | 7/2003 | Lopez |
| 6,601,721 B2 | 8/2003 | Jansen et al. |
| 6,626,309 B1 | 9/2003 | Jansen et al. |
| 6,632,201 B1 | 10/2003 | Mathias et al. |
| 6,638,244 B1 | 10/2003 | Reynolds |
| D482,121 S | 11/2003 | Harding et al. |
| D482,447 S | 11/2003 | Harding et al. |
| 6,651,956 B2 | 11/2003 | Miller |
| 6,652,509 B1 | 11/2003 | Helgren et al. |
| D483,487 S | 12/2003 | Harding et al. |
| D483,869 S | 12/2003 | Tran et al. |
| 6,656,433 B2 | 12/2003 | Sasso |
| 6,666,852 B2 | 12/2003 | Niedospial |
| 6,681,810 B2 | 1/2004 | Weston |
| 6,681,946 B1 | 1/2004 | Jansen et al. |
| 6,682,509 B2 | 1/2004 | Lopez |
| 6,692,478 B1 | 2/2004 | Paradis |
| 6,692,829 B2 | 2/2004 | Stubler et al. |
| 6,695,829 B2 | 2/2004 | Hellstrom et al. |
| 6,699,229 B2 | 3/2004 | Zinger et al. |
| 6,699,232 B2 | 3/2004 | Hart et al. |
| 6,706,022 B1 | 3/2004 | Leinsing et al. |
| 6,706,031 B2 | 3/2004 | Manera |
| 6,715,520 B2 | 4/2004 | Andreasson et al. |
| 6,729,370 B2 | 5/2004 | Norton et al. |
| 6,736,798 B2 | 5/2004 | Ohkubo et al. |
| 6,745,998 B2 | 6/2004 | Doyle |
| 6,746,438 B1 | 6/2004 | Arnissolle |
| 6,752,180 B2 | 6/2004 | Delay |
| D495,416 S | 8/2004 | Dimeo et al. |
| D496,457 S | 9/2004 | Prais et al. |
| 6,802,490 B2 | 10/2004 | Leinsing et al. |
| 6,832,994 B2 | 12/2004 | Niedospial et al. |
| 6,852,103 B2 | 2/2005 | Fowles et al. |
| 6,875,203 B1 | 4/2005 | Fowles et al. |
| 6,875,205 B2 | 4/2005 | Leinsing |
| 6,878,131 B2 | 4/2005 | Novacek et al. |
| 6,884,253 B1 | 4/2005 | Mcfarlane |
| 6,890,328 B2 | 5/2005 | Fowles et al. |
| D506,256 S | 6/2005 | Miyoshi et al. |
| 6,901,975 B2 | 6/2005 | Aramata et al. |
| 6,945,417 B2 | 9/2005 | Jansen et al. |
| 6,948,522 B2 | 9/2005 | Newbrough et al. |
| 6,949,086 B2 | 9/2005 | Ferguson et al. |
| 6,951,613 B2 | 10/2005 | Reif et al. |
| 6,953,450 B2 | 10/2005 | Baldwin et al. |
| 6,957,745 B2 | 10/2005 | Thibault et al. |
| 6,960,164 B2 | 11/2005 | O'Heeron |
| 6,964,684 B2 | 11/2005 | Ortiz et al. |
| 6,972,002 B2 | 12/2005 | Thorne |
| 6,979,318 B1 | 12/2005 | Mcdonald et al. |
| RE38,996 E | 2/2006 | Crawford et al. |
| 6,994,315 B2 | 2/2006 | Ryan et al. |
| 6,997,916 B2 | 2/2006 | Simas et al. |
| 6,997,917 B2 | 2/2006 | Niedospial et al. |
| 7,024,968 B2 | 4/2006 | Raudabough et al. |
| 7,070,589 B2 | 7/2006 | Lolachi et al. |
| 7,074,216 B2 | 7/2006 | Fowles et al. |
| 7,083,600 B2 | 8/2006 | Meloul |
| 7,086,431 B2 | 8/2006 | D'Antonio et al. |
| 7,097,637 B2 | 8/2006 | Triplett et al. |
| 7,100,890 B2 | 9/2006 | Cote et al. |
| 7,140,401 B2 | 11/2006 | Wilcox et al. |
| 7,150,735 B2 | 12/2006 | Hickle |
| 7,192,423 B2 | 3/2007 | Wong |
| 7,195,623 B2 | 3/2007 | Burroughs et al. |
| D546,450 S | 7/2007 | Wolf |
| 7,241,285 B1 | 7/2007 | Dikeman |
| 7,294,122 B2 | 11/2007 | Kubo et al. |
| 7,306,199 B2 | 12/2007 | Leinsing et al. |
| D560,815 S | 1/2008 | Tajima |
| D561,348 S | 2/2008 | Zinger et al. |

(56) References Cited

U.S. PATENT DOCUMENTS

| | | |
|---|---|---|
| 7,326,188 B1 | 2/2008 | Russell et al. |
| 7,326,194 B2 | 2/2008 | Zinger et al. |
| 7,335,213 B1 | 2/2008 | Hyde et al. |
| 7,350,764 B2 | 4/2008 | Raybuck |
| 7,354,422 B2 | 4/2008 | Riesenberger et al. |
| 7,354,427 B2 | 4/2008 | Fangrow |
| D573,250 S | 7/2008 | Macrae et al. |
| D575,314 S | 8/2008 | Hind |
| 7,425,209 B2 | 9/2008 | Fowles et al. |
| 7,435,246 B2 | 10/2008 | Zihlmann |
| D580,558 S | 11/2008 | Shigesada et al. |
| D581,529 S | 11/2008 | Moehle et al. |
| 7,452,348 B2 | 11/2008 | Hasegawa |
| 7,470,257 B2 | 12/2008 | Norton et al. |
| 7,470,265 B2 | 12/2008 | Brugger et al. |
| 7,472,932 B2 | 1/2009 | Weber et al. |
| 7,488,297 B2 | 2/2009 | Flaherty |
| 7,491,197 B2 | 2/2009 | Jansen et al. |
| 7,497,848 B2 | 3/2009 | Leinsing et al. |
| 7,500,961 B2 | 3/2009 | Nemoto |
| 7,523,967 B2 | 4/2009 | Steppe |
| 7,530,546 B2 | 5/2009 | Ryan et al. |
| D595,420 S | 6/2009 | Suzuki et al. |
| D595,421 S | 6/2009 | Suzuki et al. |
| 7,540,863 B2 | 6/2009 | Haindl |
| 7,540,865 B2 | 6/2009 | Griffin et al. |
| 7,544,191 B2 | 6/2009 | Peluso et al. |
| D595,862 S | 7/2009 | Suzuki et al. |
| D595,863 S | 7/2009 | Suzuki et al. |
| 7,569,062 B1 | 8/2009 | Kuehn et al. |
| D604,837 S | 11/2009 | Crawford et al. |
| 7,611,487 B2 | 11/2009 | Woehr et al. |
| 7,611,502 B2 | 11/2009 | Daly |
| 7,615,041 B2 | 11/2009 | Sullivan et al. |
| 7,628,779 B2 | 12/2009 | Aneas |
| 7,632,261 B2 | 12/2009 | Zinger et al. |
| D608,900 S | 1/2010 | Giraud et al. |
| D609,804 S | 2/2010 | Uchida et al. |
| 7,654,995 B2 | 2/2010 | Warren et al. |
| 7,670,326 B2 | 3/2010 | Shemesh |
| 7,695,445 B2 | 4/2010 | Yuki |
| 7,703,483 B2 | 4/2010 | Hartman et al. |
| 7,704,229 B2 | 4/2010 | Moberg et al. |
| 7,704,236 B2 | 4/2010 | Denolly |
| D616,090 S | 5/2010 | Kawamura |
| 7,713,247 B2 | 5/2010 | Lopez |
| 7,717,886 B2 | 5/2010 | Lopez |
| 7,722,090 B2 | 5/2010 | Burton et al. |
| D616,984 S | 6/2010 | Gilboa |
| 7,731,678 B2 | 6/2010 | Tennican et al. |
| 7,743,799 B2 | 6/2010 | Mosler et al. |
| 7,744,581 B2 | 6/2010 | Wallen et al. |
| 7,757,901 B2 | 7/2010 | Welp |
| 7,758,082 B2 | 7/2010 | Weigel et al. |
| 7,758,560 B2 | 7/2010 | Connell et al. |
| 7,762,524 B2 | 7/2010 | Cawthon et al. |
| 7,766,304 B2 | 8/2010 | Phillips |
| 7,771,383 B2 | 8/2010 | Truitt et al. |
| D624,641 S | 9/2010 | Boclet |
| 7,799,009 B2 | 9/2010 | Niedospial et al. |
| 7,803,140 B2 | 9/2010 | Fangrow, Jr. |
| D627,216 S | 11/2010 | Fulginiti |
| D630,732 S | 1/2011 | Lev et al. |
| 7,862,537 B2 | 1/2011 | Zinger et al. |
| 7,867,215 B2 | 1/2011 | Akerlund et al. |
| 7,879,018 B2 | 2/2011 | Zinger et al. |
| 7,883,499 B2 | 2/2011 | Fangrow |
| 7,887,583 B2 | 2/2011 | Macoviak |
| 7,895,216 B2 | 2/2011 | Longshaw et al. |
| D634,007 S | 3/2011 | Zinger et al. |
| 7,896,849 B2 | 3/2011 | Delay |
| 7,900,659 B2 | 3/2011 | Whitley et al. |
| 7,914,499 B2 | 3/2011 | Gonnelli et al. |
| D637,713 S | 5/2011 | Nord et al. |
| 7,963,954 B2 | 6/2011 | Kavazov |
| D641,080 S | 7/2011 | Zinger et al. |
| 7,985,216 B2 | 7/2011 | Daily et al. |
| D644,104 S | 8/2011 | Maeda et al. |
| 7,993,328 B2 | 8/2011 | Whitley |
| 8,007,461 B2 | 8/2011 | Huo et al. |
| 8,012,132 B2 | 9/2011 | Lum et al. |
| 8,016,809 B2 | 9/2011 | Zinger et al. |
| 8,021,325 B2 | 9/2011 | Zinger et al. |
| 8,025,653 B2 | 9/2011 | Capitaine et al. |
| 8,025,683 B2 | 9/2011 | Morrison |
| 8,029,472 B2 | 10/2011 | Leinsing et al. |
| 8,038,123 B2 | 10/2011 | Ruschke et al. |
| 8,066,688 B2 | 11/2011 | Zinger et al. |
| 8,070,739 B2 | 12/2011 | Zinger et al. |
| 8,075,550 B2 | 12/2011 | Nord et al. |
| 8,096,525 B2 | 1/2012 | Ryan |
| 8,105,314 B2 | 1/2012 | Fangrow, Jr. |
| D654,166 S | 2/2012 | Lair |
| D655,017 S | 2/2012 | Mosler et al. |
| 8,122,923 B2 | 2/2012 | Kraus et al. |
| 8,123,736 B2 | 2/2012 | Kraushaar et al. |
| D655,071 S | 3/2012 | Davila |
| D657,461 S | 4/2012 | Schembre et al. |
| 8,152,779 B2 | 4/2012 | Cabiri |
| 8,157,784 B2 | 4/2012 | Rogers |
| 8,167,863 B2 | 5/2012 | Yow |
| 8,172,824 B2 | 5/2012 | Pfeifer et al. |
| 8,177,768 B2 | 5/2012 | Leinsing |
| 8,182,452 B2 | 5/2012 | Mansour et al. |
| 8,187,248 B2 | 5/2012 | Zihlmann |
| 8,196,614 B2 | 6/2012 | Kriheli |
| 8,197,459 B2 | 6/2012 | Jansen et al. |
| 8,211,069 B2 | 7/2012 | Fangrow, Jr. |
| 8,225,959 B2 | 7/2012 | Lambrecht |
| 8,241,268 B2 | 8/2012 | Whitley |
| 8,262,628 B2 | 9/2012 | Fangrow, Jr. |
| 8,262,641 B2 | 9/2012 | Vedrine et al. |
| 8,267,127 B2 | 9/2012 | Kriheli |
| D669,980 S | 10/2012 | Lev et al. |
| 8,287,513 B2 | 10/2012 | Ellstrom et al. |
| D671,654 S | 11/2012 | Akamatsu et al. |
| 8,317,741 B2 | 11/2012 | Kraushaar |
| 8,328,784 B2 | 12/2012 | Jensen et al. |
| D673,673 S | 1/2013 | Wang |
| D674,084 S | 1/2013 | Linnenschmidt |
| D674,088 S | 1/2013 | Lev et al. |
| 8,348,898 B2 | 1/2013 | Cabiri |
| D681,230 S | 4/2013 | Mosler et al. |
| 8,418,690 B2 | 4/2013 | Power et al. |
| 8,454,573 B2 | 6/2013 | Wyatt et al. |
| 8,469,939 B2 | 6/2013 | Fangrow, Jr. |
| 8,475,404 B2 | 7/2013 | Foshee et al. |
| 8,480,645 B1 | 7/2013 | Choudhury et al. |
| 8,480,646 B2 | 7/2013 | Nord et al. |
| 8,506,548 B2 | 8/2013 | Okiyama |
| 8,511,352 B2 | 8/2013 | Kraus et al. |
| 8,512,309 B2 | 8/2013 | Shemesh et al. |
| D689,605 S | 9/2013 | Bellenoit |
| D690,009 S | 9/2013 | Schembre et al. |
| D690,418 S | 9/2013 | Rosenquist |
| 8,523,837 B2 | 9/2013 | Wiggins et al. |
| D691,264 S | 10/2013 | Dallemagne et al. |
| 8,545,476 B2 | 10/2013 | Ariagno et al. |
| 8,551,067 B2 | 10/2013 | Zinger et al. |
| 8,556,879 B2 | 10/2013 | Okiyama |
| 8,562,582 B2 | 10/2013 | Tuckwell et al. |
| 8,608,723 B2 | 12/2013 | Lev et al. |
| 8,628,508 B2 | 1/2014 | Weitzel et al. |
| 8,636,689 B2 | 1/2014 | Halili et al. |
| D703,812 S | 4/2014 | Cederschiold et al. |
| 8,684,992 B2 | 4/2014 | Sullivan et al. |
| 8,684,994 B2 | 4/2014 | Lev et al. |
| 8,752,598 B2 | 6/2014 | Denenburg et al. |
| D714,935 S | 10/2014 | Nishioka et al. |
| D717,406 S | 11/2014 | Stanley et al. |
| D717,948 S | 11/2014 | Strong et al. |
| D719,650 S | 12/2014 | Arinobe et al. |
| D720,067 S | 12/2014 | Rosenquist |
| D720,451 S | 12/2014 | Denenburg et al. |

(56) References Cited

U.S. PATENT DOCUMENTS

| | | |
|---|---|---|
| D720,452 S | 12/2014 | Jordan |
| 8,900,212 B2 | 12/2014 | Kubo |
| 8,905,994 B1 | 12/2014 | Lev et al. |
| 8,915,882 B2 | 12/2014 | Cabiri |
| D720,850 S | 1/2015 | Hsia et al. |
| 8,986,370 B2 | 3/2015 | Annest |
| 9,011,522 B2 | 4/2015 | Annest |
| D732,660 S | 6/2015 | Ohashi |
| D732,664 S | 6/2015 | Woehr et al. |
| D733,291 S | 6/2015 | Wang |
| D733,292 S | 6/2015 | Rogers |
| D733,293 S | 6/2015 | Rogers |
| 9,072,827 B2 | 7/2015 | Cabiri |
| D738,494 S | 9/2015 | Kashmirian |
| D741,457 S | 10/2015 | Guest |
| 9,149,575 B2 | 10/2015 | Cabiri |
| D750,235 S | 2/2016 | Maurice |
| 9,254,242 B2 | 2/2016 | Mueller et al. |
| D757,933 S | 5/2016 | Lev et al. |
| 9,393,365 B2 | 7/2016 | Cabiri |
| D765,837 S | 9/2016 | Lev et al. |
| D767,124 S | 9/2016 | Lev et al. |
| 9,486,391 B2 | 11/2016 | Shemesh |
| 9,492,610 B2 | 11/2016 | Cabiri |
| 9,511,190 B2 | 12/2016 | Cabiri |
| 9,522,234 B2 | 12/2016 | Cabiri |
| D794,183 S | 8/2017 | Lev et al. |
| 9,763,855 B2 | 9/2017 | Fangrow |
| D833,599 S | 11/2018 | Nilsson et al. |
| D836,324 S | 12/2018 | Michalski |
| 10,206,854 B2 | 2/2019 | Wu et al. |
| D849,936 S | 5/2019 | Allard |
| D851,240 S | 6/2019 | Baid |
| 10,413,662 B2 | 9/2019 | Yeh et al. |
| D881,389 S | 4/2020 | Wang et al. |
| D881,390 S | 4/2020 | Wang et al. |
| 10,772,798 B2 | 9/2020 | Lev et al. |
| D903,836 S | 12/2020 | Pak et al. |
| D923,782 S | 6/2021 | Lev et al. |
| D923,812 S | 6/2021 | Ben Shalom |
| 2001/0000347 A1 | 4/2001 | Hellstrom et al. |
| 2001/0025671 A1 | 10/2001 | Safabash |
| 2001/0029360 A1 | 10/2001 | Miyoshi et al. |
| 2001/0047150 A1 | 11/2001 | Chobotov |
| 2001/0051793 A1 | 12/2001 | Weston |
| 2002/0017328 A1 | 2/2002 | Loo |
| 2002/0029080 A1 | 3/2002 | Mortier et al. |
| 2002/0055711 A1 | 5/2002 | Lavi et al. |
| 2002/0065488 A1 | 5/2002 | Suzuki et al. |
| 2002/0066715 A1 | 6/2002 | Niedospial |
| 2002/0087118 A1 | 7/2002 | Reynolds et al. |
| 2002/0087141 A1 | 7/2002 | Zinger et al. |
| 2002/0087144 A1 | 7/2002 | Zinger et al. |
| 2002/0104584 A1 | 8/2002 | Spero et al. |
| 2002/0115980 A1 | 8/2002 | Niedospial et al. |
| 2002/0121496 A1 | 9/2002 | Thiebault et al. |
| 2002/0123736 A1 | 9/2002 | Fowles et al. |
| 2002/0123737 A1 | 9/2002 | Hart et al. |
| 2002/0127150 A1 | 9/2002 | Sasso |
| 2002/0128628 A1 | 9/2002 | Fathallah |
| 2002/0138045 A1 | 9/2002 | Moen |
| 2002/0173752 A1 | 11/2002 | Polzin |
| 2002/0193777 A1 | 12/2002 | Aneas |
| 2003/0028156 A1 | 2/2003 | Juliar |
| 2003/0036725 A1 | 2/2003 | Lavi et al. |
| 2003/0068354 A1 | 4/2003 | Reif et al. |
| 2003/0069550 A1 | 4/2003 | Sharp |
| 2003/0073971 A1 | 4/2003 | Saker |
| 2003/0083742 A1 | 5/2003 | Spence et al. |
| 2003/0100866 A1 | 5/2003 | Reynolds |
| 2003/0109846 A1 | 6/2003 | Zinger et al. |
| 2003/0120209 A1 | 6/2003 | Jensen et al. |
| 2003/0135159 A1 | 7/2003 | Daily et al. |
| 2003/0153895 A1 | 8/2003 | Leinsing |
| 2003/0187420 A1 | 10/2003 | Akerlund et al. |
| 2003/0191445 A1 | 10/2003 | Wallen et al. |
| 2003/0195479 A1 | 10/2003 | Kuracina et al. |
| 2003/0199827 A1 | 10/2003 | Thorne |
| 2003/0199846 A1 | 10/2003 | Fowles et al. |
| 2003/0199847 A1 | 10/2003 | Akerlund et al. |
| 2003/0205843 A1 | 11/2003 | Adams |
| 2003/0236543 A1 | 12/2003 | Brenneman et al. |
| 2004/0010207 A1 | 1/2004 | Flaherty et al. |
| 2004/0024354 A1 | 2/2004 | Reynolds |
| 2004/0039365 A1 | 2/2004 | Aramata et al. |
| 2004/0044327 A1 | 3/2004 | Hasegawa |
| 2004/0044406 A1 | 3/2004 | Woolfson et al. |
| 2004/0073189 A1 | 4/2004 | Wyatt et al. |
| 2004/0143218 A1 | 7/2004 | Das |
| 2004/0143226 A1 | 7/2004 | Marsden |
| 2004/0153047 A1 | 8/2004 | Blank et al. |
| 2004/0158172 A1 | 8/2004 | Hancock |
| 2004/0162515 A1 | 8/2004 | Chornenky et al. |
| 2004/0162540 A1 | 8/2004 | Walenciak et al. |
| 2004/0167472 A1 | 8/2004 | Howell et al. |
| 2004/0167620 A1 | 8/2004 | Ortiz et al. |
| 2004/0181192 A1 | 9/2004 | Cuppy |
| 2004/0186424 A1 | 9/2004 | Hjertman |
| 2004/0199139 A1 | 10/2004 | Fowles et al. |
| 2004/0204699 A1 | 10/2004 | Hanly et al. |
| 2004/0217315 A1 | 11/2004 | Doyle |
| 2004/0225274 A1 | 11/2004 | Jansen et al. |
| 2004/0236305 A1 | 11/2004 | Jansen et al. |
| 2004/0236419 A1 | 11/2004 | Milo |
| 2004/0249341 A1 | 12/2004 | Newbrough et al. |
| 2004/0255952 A1 | 12/2004 | Carlsen et al. |
| 2005/0010287 A1 | 1/2005 | Macoviak et al. |
| 2005/0015070 A1 | 1/2005 | Delnevo et al. |
| 2005/0016626 A1 | 1/2005 | Wilcox et al. |
| 2005/0049553 A1 | 3/2005 | Triplett et al. |
| 2005/0055008 A1 | 3/2005 | Paradis et al. |
| 2005/0070999 A1 | 3/2005 | Spence |
| 2005/0075727 A1 | 4/2005 | Wheatley |
| 2005/0082828 A1 | 4/2005 | Wicks et al. |
| 2005/0124964 A1 | 6/2005 | Niedospial et al. |
| 2005/0137523 A1 | 6/2005 | Wyatt et al. |
| 2005/0137566 A1 | 6/2005 | Fowles et al. |
| 2005/0137702 A1 | 6/2005 | Haug et al. |
| 2005/0148994 A1 | 7/2005 | Leinsing |
| 2005/0159706 A1 | 7/2005 | Wilkinson et al. |
| 2005/0159724 A1 | 7/2005 | Enerson |
| 2005/0182383 A1 | 8/2005 | Wallen |
| 2005/0209554 A1 | 9/2005 | Landau |
| 2005/0261637 A1 | 11/2005 | Miller |
| 2005/0277896 A1 | 12/2005 | Messerli et al. |
| 2006/0030832 A1 | 2/2006 | Niedospial et al. |
| 2006/0049209 A1 | 3/2006 | Baker |
| 2006/0058741 A1 | 3/2006 | Gallagher |
| 2006/0074484 A1 | 4/2006 | Huber |
| 2006/0079834 A1 | 4/2006 | Tennican et al. |
| 2006/0089594 A1 | 4/2006 | Landau |
| 2006/0089603 A1 | 4/2006 | Truitt et al. |
| 2006/0095015 A1 | 5/2006 | Hobbs et al. |
| 2006/0106360 A1 | 5/2006 | Wong |
| 2006/0135948 A1 | 6/2006 | Varma |
| 2006/0155257 A1 | 7/2006 | Reynolds |
| 2006/0161192 A1 | 7/2006 | Young |
| 2006/0169348 A1 | 8/2006 | Yigal |
| 2006/0173410 A1 | 8/2006 | Moberg et al. |
| 2006/0178646 A1 | 8/2006 | Harris et al. |
| 2006/0195029 A1 | 8/2006 | Shults et al. |
| 2006/0212004 A1 | 9/2006 | Atil |
| 2006/0224105 A1 | 10/2006 | Thorne et al. |
| 2006/0253084 A1 | 11/2006 | Nordgren |
| 2006/0259004 A1 | 11/2006 | Connell et al. |
| 2006/0259135 A1 | 11/2006 | Navia et al. |
| 2007/0016381 A1 | 1/2007 | Kamath et al. |
| 2007/0024995 A1 | 2/2007 | Hayashi |
| 2007/0060904 A1 | 3/2007 | Vedrine et al. |
| 2007/0078428 A1 | 4/2007 | Reynolds et al. |
| 2007/0079894 A1 | 4/2007 | Kraus et al. |
| 2007/0083164 A1 | 4/2007 | Barrelle et al. |
| 2007/0088252 A1 | 4/2007 | Pestotnik et al. |
| 2007/0088293 A1 | 4/2007 | Fangrow |

(56) References Cited

U.S. PATENT DOCUMENTS

| | | |
|---|---|---|
| 2007/0088313 A1 | 4/2007 | Zinger et al. |
| 2007/0095856 A1 | 5/2007 | Vogel et al. |
| 2007/0106218 A1 | 5/2007 | Yodfat et al. |
| 2007/0106244 A1 | 5/2007 | Mosler et al. |
| 2007/0112324 A1 | 5/2007 | Hamedi-Sangsari |
| 2007/0156112 A1 | 7/2007 | Walsh |
| 2007/0167904 A1 | 7/2007 | Zinger et al. |
| 2007/0167912 A1 | 7/2007 | Causey et al. |
| 2007/0191760 A1 | 8/2007 | Iguchi et al. |
| 2007/0191764 A1 | 8/2007 | Zihlmann |
| 2007/0191767 A1 | 8/2007 | Hennessy et al. |
| 2007/0203451 A1 | 8/2007 | Murakami et al. |
| 2007/0219483 A1 | 9/2007 | Kitani et al. |
| 2007/0244447 A1 | 10/2007 | Capitaine et al. |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0249995 A1 | 10/2007 | Van |
| 2007/0255202 A1 | 11/2007 | Kitani et al. |
| 2007/0265574 A1 | 11/2007 | Tennican et al. |
| 2007/0265581 A1 | 11/2007 | Funamura et al. |
| 2007/0270778 A9 | 11/2007 | Zinger et al. |
| 2007/0287953 A1 | 12/2007 | Ziv et al. |
| 2007/0299404 A1 | 12/2007 | Katoh et al. |
| 2008/0009789 A1 | 1/2008 | Zinger et al. |
| 2008/0009822 A1 | 1/2008 | Enerson |
| 2008/0015496 A1 | 1/2008 | Hamedi-Sangsari |
| 2008/0039935 A1 | 2/2008 | Buch et al. |
| 2008/0077235 A1 | 3/2008 | Kirson |
| 2008/0125860 A1 | 5/2008 | Webler et al. |
| 2008/0135051 A1 | 6/2008 | Lee |
| 2008/0167713 A1 | 7/2008 | Bolling |
| 2008/0172024 A1 | 7/2008 | Yow |
| 2008/0188799 A1 | 8/2008 | Mueller-Beckhaus et al. |
| 2008/0195049 A1 | 8/2008 | Thalmann et al. |
| 2008/0208138 A1 | 8/2008 | Lim et al. |
| 2008/0215015 A1 | 9/2008 | Cindrich et al. |
| 2008/0249473 A1 | 10/2008 | Rutti et al. |
| 2008/0249479 A1 | 10/2008 | Zinger et al. |
| 2008/0249498 A1 | 10/2008 | Fangrow |
| 2008/0262465 A1 | 10/2008 | Zinger et al. |
| 2008/0262609 A1 | 10/2008 | Gross et al. |
| 2008/0269687 A1 | 10/2008 | Chong et al. |
| 2008/0275407 A1 | 11/2008 | Scheurer |
| 2008/0287905 A1 | 11/2008 | Hiejima et al. |
| 2008/0294100 A1 | 11/2008 | De et al. |
| 2008/0306439 A1 | 12/2008 | Nelson et al. |
| 2008/0312634 A1 | 12/2008 | Helmerson et al. |
| 2009/0012492 A1 | 1/2009 | Zihlmann |
| 2009/0043253 A1 | 2/2009 | Podaima |
| 2009/0054834 A1 | 2/2009 | Zinger et al. |
| 2009/0054852 A1 | 2/2009 | Takano et al. |
| 2009/0054969 A1 | 2/2009 | Salahieh et al. |
| 2009/0062767 A1 | 3/2009 | Van et al. |
| 2009/0076360 A1 | 3/2009 | Brister et al. |
| 2009/0082750 A1 | 3/2009 | Denenburg et al. |
| 2009/0139724 A1 | 6/2009 | Gray et al. |
| 2009/0143758 A1 | 6/2009 | Okiyama |
| 2009/0177177 A1 | 7/2009 | Zinger et al. |
| 2009/0177178 A1 | 7/2009 | Pedersen |
| 2009/0187140 A1 | 7/2009 | Racz |
| 2009/0216103 A1 | 8/2009 | Brister et al. |
| 2009/0216212 A1 | 8/2009 | Fangrow, Jr. |
| 2009/0257306 A1 | 10/2009 | Coffeen et al. |
| 2009/0267011 A1 | 10/2009 | Hatton et al. |
| 2009/0299325 A1 | 12/2009 | Vedrine et al. |
| 2009/0318946 A1 | 12/2009 | Tamesada |
| 2009/0326506 A1 | 12/2009 | Hasegawa et al. |
| 2010/0010443 A1 | 1/2010 | Morgan et al. |
| 2010/0016811 A1 | 1/2010 | Smith |
| 2010/0022985 A1 | 1/2010 | Sullivan et al. |
| 2010/0030181 A1 | 2/2010 | Helle et al. |
| 2010/0036319 A1 | 2/2010 | Drake et al. |
| 2010/0042147 A1 | 2/2010 | Janovsky et al. |
| 2010/0049315 A1 | 2/2010 | Kirson |
| 2010/0070027 A1 | 3/2010 | Bonhoeffer et al. |
| 2010/0076397 A1 | 3/2010 | Reed et al. |
| 2010/0087786 A1 | 4/2010 | Zinger et al. |
| 2010/0137827 A1 | 6/2010 | Warren et al. |
| 2010/0137831 A1 | 6/2010 | Tsais |
| 2010/0152658 A1 | 6/2010 | Hanson et al. |
| 2010/0160889 A1 | 6/2010 | Smith et al. |
| 2010/0161047 A1 | 6/2010 | Cabiri |
| 2010/0162548 A1 | 7/2010 | Leidig |
| 2010/0168664 A1 | 7/2010 | Zinger et al. |
| 2010/0168712 A1 | 7/2010 | Tuckwell et al. |
| 2010/0179506 A1 | 7/2010 | Shemesh et al. |
| 2010/0198148 A1 | 8/2010 | Zinger et al. |
| 2010/0204670 A1 | 8/2010 | Kraushaar et al. |
| 2010/0228220 A1 | 9/2010 | Zinger et al. |
| 2010/0241088 A1 | 9/2010 | Ranalletta et al. |
| 2010/0262232 A1 | 10/2010 | Annest |
| 2010/0274184 A1 | 10/2010 | Chun |
| 2010/0274202 A1 | 10/2010 | Hyde et al. |
| 2010/0286661 A1 | 11/2010 | Raday et al. |
| 2010/0305548 A1 | 12/2010 | Kraushaar |
| 2010/0312220 A1 | 12/2010 | Kalitzki |
| 2011/0004143 A1 | 1/2011 | Beiriger et al. |
| 2011/0004184 A1 | 1/2011 | Proksch et al. |
| 2011/0044850 A1 | 2/2011 | Solomon et al. |
| 2011/0054440 A1 | 3/2011 | Lewis |
| 2011/0087164 A1 | 4/2011 | Mosier et al. |
| 2011/0125056 A1 | 5/2011 | Merchant |
| 2011/0144584 A1 | 6/2011 | Wozencroft |
| 2011/0160655 A1 | 6/2011 | Hanson et al. |
| 2011/0160701 A1 | 6/2011 | Wyatt et al. |
| 2011/0172636 A1 | 7/2011 | Aasmul |
| 2011/0175347 A1 | 7/2011 | Okiyama |
| 2011/0178493 A1 | 7/2011 | Okiyama |
| 2011/0218511 A1 | 9/2011 | Yokoyama |
| 2011/0224640 A1 | 9/2011 | Kuehn et al. |
| 2011/0230856 A1 | 9/2011 | Kyle et al. |
| 2011/0264037 A1 | 10/2011 | Foshee et al. |
| 2011/0264069 A1 | 10/2011 | Bochenko |
| 2011/0275988 A1 | 11/2011 | Davis et al. |
| 2011/0276007 A1 | 11/2011 | Denenburg |
| 2011/0319827 A1 | 12/2011 | Leinsing et al. |
| 2012/0022344 A1 | 1/2012 | Kube |
| 2012/0022469 A1 | 1/2012 | Alpert |
| 2012/0053555 A1 | 3/2012 | Ariagno et al. |
| 2012/0059332 A1 | 3/2012 | Woehr et al. |
| 2012/0059346 A1 | 3/2012 | Sheppard et al. |
| 2012/0067429 A1 | 3/2012 | Mosler et al. |
| 2012/0071819 A1 | 3/2012 | Brueggemann et al. |
| 2012/0078214 A1 | 3/2012 | Finke et al. |
| 2012/0123382 A1 | 5/2012 | Kubo |
| 2012/0184938 A1 | 7/2012 | Lev et al. |
| 2012/0215182 A1 | 8/2012 | Mansour et al. |
| 2012/0220977 A1 | 8/2012 | Yow |
| 2012/0220978 A1 | 8/2012 | Lev et al. |
| 2012/0265163 A1 | 10/2012 | Cheng et al. |
| 2012/0271229 A1 | 10/2012 | Lev et al. |
| 2012/0296307 A1 | 11/2012 | Holt et al. |
| 2012/0310203 A1 | 12/2012 | Khaled et al. |
| 2012/0323172 A1 | 12/2012 | Lev et al. |
| 2012/0323187 A1 | 12/2012 | Iwase et al. |
| 2012/0323210 A1 | 12/2012 | Lev et al. |
| 2013/0046269 A1 | 2/2013 | Lev et al. |
| 2013/0053814 A1 | 2/2013 | Mueller-Beckhaus et al. |
| 2013/0096493 A1 | 4/2013 | Kubo et al. |
| 2013/0110049 A1 | 5/2013 | Cronenberg et al. |
| 2013/0144248 A1 | 6/2013 | Putter et al. |
| 2013/0199669 A1 | 8/2013 | Moy et al. |
| 2013/0226100 A1 | 8/2013 | Lev |
| 2013/0231630 A1 | 9/2013 | Kraus et al. |
| 2013/0237904 A1 | 9/2013 | Deneburg et al. |
| 2013/0253448 A1 | 9/2013 | Baron et al. |
| 2013/0289530 A1 | 10/2013 | Wyatt et al. |
| 2013/0315026 A1 | 11/2013 | Cheio et al. |
| 2013/0317472 A1 | 11/2013 | Finke |
| 2014/0020793 A1 | 1/2014 | Denenburg et al. |
| 2014/0096862 A1 | 4/2014 | Aneas |
| 2014/0102552 A1 | 4/2014 | Shemesh |
| 2014/0150911 A1 | 6/2014 | Hanner et al. |

(56) References Cited

U.S. PATENT DOCUMENTS

| | | |
|---|---|---|
| 2014/0194854 A1 | 7/2014 | Tsais |
| 2014/0221940 A1 | 8/2014 | Clauson et al. |
| 2014/0276215 A1 | 9/2014 | Nelson et al. |
| 2014/0277052 A1 | 9/2014 | Haselby et al. |
| 2014/0352845 A1 | 12/2014 | Lev et al. |
| 2015/0082746 A1 | 3/2015 | Ivosevic et al. |
| 2015/0088078 A1 | 3/2015 | Lev et al. |
| 2015/0112297 A1 | 4/2015 | Lev et al. |
| 2015/0209230 A1 | 7/2015 | Lev et al. |
| 2015/0250681 A1 | 9/2015 | Lev et al. |
| 2015/0290390 A1 | 10/2015 | Ring et al. |
| 2015/0297839 A1 | 10/2015 | Sanders et al. |
| 2015/0297880 A1 | 10/2015 | Ogawa et al. |
| 2015/0305770 A1 | 10/2015 | Fill et al. |
| 2016/0081308 A1 | 3/2016 | Cary et al. |
| 2016/0081878 A1 | 3/2016 | Marks et al. |
| 2016/0088995 A1 | 3/2016 | Ueda et al. |
| 2016/0166824 A1 | 6/2016 | Lev et al. |
| 2016/0199569 A1 | 7/2016 | Yevmenenko et al. |
| 2016/0228644 A1 | 8/2016 | Cabiri |
| 2016/0287475 A1 | 10/2016 | Yevmenenko et al. |
| 2016/0367439 A1 | 12/2016 | Davis et al. |
| 2018/0008513 A1 | 1/2018 | Iibuchi et al. |
| 2018/0161243 A1 | 6/2018 | Ariagno et al. |
| 2018/0221572 A1 | 8/2018 | Schlitt et al. |
| 2018/0303720 A1 | 10/2018 | Kennard et al. |
| 2019/0083357 A1 | 3/2019 | David et al. |
| 2019/0117514 A1 | 4/2019 | Denenburg et al. |
| 2019/0133885 A1 | 5/2019 | Wu et al. |
| 2019/0343725 A1 | 11/2019 | Denenburg |
| 2020/0093692 A1 | 3/2020 | Lev et al. |
| 2020/0276084 A1 | 9/2020 | Denenburg |
| 2020/0282133 A1 | 9/2020 | Mason et al. |
| 2020/0330326 A1 | 10/2020 | Merchant et al. |
| 2020/0376194 A1 | 12/2020 | Fabrikant et al. |

FOREIGN PATENT DOCUMENTS

| | | |
|---|---|---|
| CN | 1747683 A | 3/2006 |
| CN | 1863566 A | 11/2006 |
| CN | 1950049 A | 4/2007 |
| CN | 101001661 A | 7/2007 |
| CN | 101687083 A | 3/2010 |
| CN | 106413799 A | 2/2017 |
| CN | 306375580 S | 3/2021 |
| DE | 1064693 B | 9/1959 |
| DE | 1913926 A1 | 9/1970 |
| DE | 4122476 A1 | 1/1993 |
| DE | 4314657 A1 | 11/1994 |
| DE | 4408498 A1 | 5/1995 |
| DE | 19504413 A1 | 8/1996 |
| DE | 202004012714 U1 | 11/2004 |
| DE | 102007046951 B3 | 2/2009 |
| DE | 202009011019 U1 | 12/2010 |
| EM | 001126270-0001 | 8/2010 |
| EM | 001680703-0001 | 8/2010 |
| EM | 001680703-0002 | 8/2010 |
| EM | 002446062-0001 | 8/2010 |
| EM | 002446062-0002 | 8/2010 |
| EM | 000627237-0001 | 10/2010 |
| EM | 006630893-0001 | 8/2019 |
| EM | 008039507-0004 | 1/2021 |
| EP | 0192661 A1 | 9/1986 |
| EP | 0195018 A1 | 9/1986 |
| EP | 0258913 A2 | 3/1988 |
| EP | 0416454 A2 | 3/1991 |
| EP | 0426403 A1 | 5/1991 |
| EP | 0282545 B1 | 2/1992 |
| EP | 0518397 A1 | 12/1992 |
| EP | 0521460 A1 | 1/1993 |
| EP | 0582038 A2 | 2/1994 |
| EP | 0598918 A1 | 6/1994 |
| EP | 0637443 A1 | 2/1995 |
| EP | 0737467 A1 | 10/1996 |
| EP | 0761562 A1 | 3/1997 |
| EP | 0765652 A1 | 4/1997 |
| EP | 0765853 A1 | 4/1997 |
| EP | 0806597 A1 | 11/1997 |
| EP | 0814866 A1 | 1/1998 |
| EP | 0829248 A2 | 3/1998 |
| EP | 0856331 A2 | 8/1998 |
| EP | 0882441 A2 | 12/1998 |
| EP | 0887085 A2 | 12/1998 |
| EP | 0887885 A2 | 12/1998 |
| EP | 0897708 A2 | 2/1999 |
| EP | 0898951 A2 | 3/1999 |
| EP | 0960616 A2 | 12/1999 |
| EP | 1008337 A1 | 6/2000 |
| EP | 1029526 A1 | 8/2000 |
| EP | 1034809 A1 | 9/2000 |
| EP | 1051988 A2 | 11/2000 |
| EP | 1323403 A1 | 7/2003 |
| EP | 1329210 A1 | 7/2003 |
| EP | 1396250 A1 | 3/2004 |
| EP | 1454609 A1 | 9/2004 |
| EP | 1454650 A1 | 9/2004 |
| EP | 1498097 A2 | 1/2005 |
| EP | 1872824 A1 | 1/2008 |
| EP | 1911432 A1 | 4/2008 |
| EP | 1919432 A1 | 5/2008 |
| EP | 1930038 A2 | 6/2008 |
| EP | 2090278 A1 | 8/2009 |
| EP | 2351548 A1 | 8/2011 |
| EP | 2351549 A1 | 8/2011 |
| EP | 2462913 A1 | 6/2012 |
| EP | 2512399 A1 | 10/2012 |
| EP | 2416739 B1 | 6/2016 |
| FR | 2029242 A5 | 10/1970 |
| FR | 2856660 A1 | 12/2004 |
| FR | 2869795 A1 | 11/2005 |
| FR | 2931363 A1 | 11/2009 |
| GB | 1444210 A | 7/1976 |
| IL | 171662 | 10/2005 |
| IL | 186290 | 1/2008 |
| JP | 03-062426 B2 | 9/1991 |
| JP | 03-205560 A | 9/1991 |
| JP | 04-329954 A | 11/1992 |
| JP | 06-050656 U | 7/1994 |
| JP | 08-000710 A | 1/1996 |
| JP | 09-104460 A | 4/1997 |
| JP | 09-104461 A | 4/1997 |
| JP | 10-118158 A | 5/1998 |
| JP | 10-504736 A | 5/1998 |
| JP | 11-503627 A | 3/1999 |
| JP | 11-319031 A | 11/1999 |
| JP | 2000-508934 A | 7/2000 |
| JP | 2000-237278 A | 9/2000 |
| JP | 2000-262497 A | 9/2000 |
| JP | 2001-505083 A | 4/2001 |
| JP | 2002-035140 A | 2/2002 |
| JP | 2002-516160 A | 6/2002 |
| JP | 2002-355318 A | 12/2002 |
| JP | 2003-033441 A | 2/2003 |
| JP | 2003-102807 A | 4/2003 |
| JP | 2003-513709 A | 4/2003 |
| JP | 2004-501721 A | 1/2004 |
| JP | 2004-097253 A | 4/2004 |
| JP | 2004-522541 A | 7/2004 |
| JP | 2004-267776 A | 9/2004 |
| JP | 2005-270629 A | 10/2005 |
| JP | 2005-537048 A | 12/2005 |
| JP | 2006-061421 A | 3/2006 |
| JP | 2008-220961 A | 9/2008 |
| JP | 2009-513294 A | 4/2009 |
| JP | 4329954 B2 | 9/2009 |
| JP | 2010-063622 A | 3/2010 |
| JP | 2010-179128 A | 8/2010 |
| JP | 2012-205769 A | 10/2012 |
| JP | 2013-520272 A | 6/2013 |
| JP | 2014-000220 A | 1/2014 |
| JP | 2015-211763 A | 11/2015 |
| JP | 2019-015749 A | 1/2019 |
| WO | 86/01487 A1 | 3/1986 |
| WO | 86/01712 A1 | 3/1986 |

(56) References Cited

FOREIGN PATENT DOCUMENTS

| | | |
|---|---|---|
| WO | 86/05683 A1 | 10/1986 |
| WO | 90/03536 A1 | 4/1990 |
| WO | 94/03373 A1 | 2/1994 |
| WO | 95/07066 A1 | 3/1995 |
| WO | 95/07720 A1 | 3/1995 |
| WO | 95/13785 A1 | 5/1995 |
| WO | 96/00053 A1 | 1/1996 |
| WO | 96/09083 A1 | 3/1996 |
| WO | 96/29113 A1 | 9/1996 |
| WO | 97/36636 A1 | 10/1997 |
| WO | 98/32411 A1 | 7/1998 |
| WO | 98/37854 A1 | 9/1998 |
| WO | 99/61093 A1 | 12/1999 |
| WO | 01/02490 A1 | 1/2001 |
| WO | 01/28490 A1 | 4/2001 |
| WO | 01/30425 A1 | 5/2001 |
| WO | 01/32524 A1 | 5/2001 |
| WO | 01/60311 A1 | 8/2001 |
| WO | 01/89607 A2 | 11/2001 |
| WO | 01/91693 A2 | 12/2001 |
| WO | 02/02165 A2 | 1/2002 |
| WO | 02/09797 A1 | 2/2002 |
| WO | 02/32372 A1 | 4/2002 |
| WO | 02/36191 A2 | 5/2002 |
| WO | 02/66100 A2 | 8/2002 |
| WO | 02/89900 A1 | 11/2002 |
| WO | 03/51423 A2 | 6/2003 |
| WO | 03/70147 A2 | 8/2003 |
| WO | 03/79956 A1 | 10/2003 |
| WO | 2004/004806 A1 | 1/2004 |
| WO | 2004/041148 A1 | 5/2004 |
| WO | 2004/096113 A2 | 11/2004 |
| WO | 2005/002492 A1 | 1/2005 |
| WO | 2005/018703 A2 | 3/2005 |
| WO | 2005/041846 A2 | 5/2005 |
| WO | 2005/105014 A1 | 11/2005 |
| WO | 2005/120431 A1 | 12/2005 |
| WO | 2006/099441 A2 | 9/2006 |
| WO | 2006/124634 A1 | 11/2006 |
| WO | 2007/015233 A1 | 2/2007 |
| WO | 2007/017868 A1 | 2/2007 |
| WO | 2007/052252 A1 | 5/2007 |
| WO | 2007/079305 A2 | 7/2007 |
| WO | 2007/101772 A1 | 9/2007 |
| WO | 2007/105221 A1 | 9/2007 |
| WO | 2007/130809 A2 | 11/2007 |
| WO | 2008/068756 A2 | 6/2008 |
| WO | 2008/076459 A1 | 6/2008 |
| WO | 2008/081424 A2 | 7/2008 |
| WO | 2008/126090 A1 | 10/2008 |
| WO | 2008/135989 A1 | 11/2008 |
| WO | 2009/026443 A2 | 2/2009 |
| WO | 2009/029010 A1 | 3/2009 |
| WO | 2009/038860 A2 | 3/2009 |
| WO | 2009/040804 A2 | 4/2009 |
| WO | 2009/087572 A1 | 7/2009 |
| WO | 2009/093249 A1 | 7/2009 |
| WO | 2009/112489 A1 | 9/2009 |
| WO | 2009/140511 A1 | 11/2009 |
| WO | 2009/146088 A1 | 12/2009 |
| WO | 2010/061743 A1 | 6/2010 |
| WO | 2010/078227 A1 | 7/2010 |
| WO | 2010/117471 A2 | 10/2010 |
| WO | 2010/117580 A1 | 10/2010 |
| WO | 2011/004360 A1 | 1/2011 |
| WO | 2011/024725 A1 | 3/2011 |
| WO | 2011/025719 A1 | 3/2011 |
| WO | 2011/039747 A1 | 4/2011 |
| WO | 2011/058545 A1 | 5/2011 |
| WO | 2011/058548 A1 | 5/2011 |
| WO | 2011/077434 A1 | 6/2011 |
| WO | 2011/090955 A1 | 7/2011 |
| WO | 2011/104711 A1 | 9/2011 |
| WO | 2011/132657 A1 | 10/2011 |
| WO | 2011/150037 A1 | 12/2011 |
| WO | 2011/156373 A1 | 12/2011 |
| WO | 2012/004784 A1 | 1/2012 |
| WO | 2012/004790 A2 | 1/2012 |
| WO | 2012/063230 A1 | 5/2012 |
| WO | 2012/143921 A1 | 10/2012 |
| WO | 2012/150587 A1 | 11/2012 |
| WO | 2013/001525 A1 | 1/2013 |
| WO | 2013/127813 A1 | 9/2013 |
| WO | 2013/134246 A1 | 9/2013 |
| WO | 2013/148435 A1 | 10/2013 |
| WO | 2013/156944 A1 | 10/2013 |
| WO | 2013/156994 A1 | 10/2013 |
| WO | 2014/033706 A2 | 3/2014 |
| WO | 2014/033710 A1 | 3/2014 |
| WO | 2014/099395 A1 | 6/2014 |
| WO | 2014/170888 A1 | 10/2014 |
| WO | 2014/174278 A1 | 10/2014 |
| WO | 2015/009746 A2 | 1/2015 |
| WO | 2015/019343 A1 | 2/2015 |
| WO | 2016/023590 A1 | 2/2016 |
| WO | 2017/203512 A1 | 11/2017 |
| WO | 2018/104930 A1 | 6/2018 |
| WO | 2018/104932 A1 | 6/2018 |
| WO | 2018/178971 A1 | 10/2018 |
| WO | WO-2020222220 A1 * 11/2020 | ............ A61J 1/2058 |

OTHER PUBLICATIONS

U.S. Appl. No. 14/784,300 by Lev, filed Oct. 14, 2015.
U.S. Appl. No. 14/888,590 by Marks, filed Nov. 2, 2015.
U.S. Appl. No. 29/438,134 by Lev, filed Nov. 27, 2012.
U.S. Appl. No. 29/438,141 by Gilboa, filed Nov. 27, 2012.
U.S. Appl. No. 29/478,723 by Lev, filed Jan. 8, 2014.
U.S. Appl. No. 29/478,726 by Lev, filed Jan. 8, 2014.
U.S. Appl. No. 29/502,037 by Lev, filed Sep. 11, 2014.
U.S. Appl. No. 29/502,053 by Lev, filed Sep. 11, 2014.
U.S. Appl. No. 29/544,969 by Ben Shalom, filed Nov. 9, 2015.
Vial-Mate Adapter Device, Baxter, May 2017, downloaded from web page:http://www.baxtermedicationdeliveryproducts.com/drug-delivery/vialmate.html, Download Date: Jul. 28, 2017, original posting date: unknown, 1page.
Vial2Bag DC, downloaded from webpage: https://www.youtube.com/watch?v=FEOkg1xNBrs, Original posting date: Aug. 21, 2014, 1 page.
West Vial2Bag DC system, Oct. 2, 2014, https://web.archive.org/web/2014002065133/http://www.westpharma.com/en/products/Pages/Reconstitutionsystems.aspx.
Written Opinion dated Aug. 16, 2012 in Int'l Application No. PCT/IL2012/000164.
Written Opinion dated Jul. 31, 2013 in Int'l Application No. PCT/IL2013/050313.
Written Opinion dated Jun. 5, 2013 in Int'l Application No. PCT/IL2012/050407.
Written Opinion of ISR dated Jun. 19, 2006 in Int'l Application No. PCT/IL2005/000376.
Written Opinion of the Int'l Searching Authority dated Oct. 27, 2008 in Int'l Application No. PCT/US2008/070024.
Written Opinion of the ISR dated Oct. 17, 2009 in Int'l Application No. PCT/IL08/00517.
YouTube, "ADVCARE—Vial Direct to bag Spoke", first available Oct. 31, 2018 (https://www.youtube.com/watch?v=dd8ctggkrfM&feature=emb_title)(2018).
YouTube, "vial2Bag DC", first available Feb. 1, 2018, (https://www.youtube.com/watch?v=abSKPo5e_Hg) (Year:2018).
YouTube, "Vial2Bag.RTM. Needleless IV Transfer System from Helapet Ltd", first available Aug. 21, 2014 (https://www.youtube.com/watch?v=yFejsv0eemE) (Year: 2014).
Author unknown, Progressive Medical inc. is proud to announce the launch of West's VIAL2BAG AGVANCED, Progressive Medinc., [Post Date Oct. 23, 2020], [Site seen Jan. 25, 2022], Seen at URL: https://www.progressivemedinc.com/west-launches-vial2bag-advanced-20mm-admixture-device/ (Year: 2020).
Our Vial2Bag Advanced™ 20mm admixture device, West Pharma, WestPharma @twitter, [Postdate Mar. 19, 2021], [Siteseen Jan. 25, 2022], Seen at URL: https://twitter.com/westpharma/status/137292105//66739971 (Year: 2021).

(56) References Cited

OTHER PUBLICATIONS

Vial2Bag Advanced™ 20mm Admixture , West Pharmaceutical Services Inc, Youtube, [post date Nov. 5, 2020], [Site seen Jan. 25, 2022], Seen at URL: https://www.youtube.com/watch?v=J0Am3mt5vn8 (Year: 2020).
Office Action dated Jun. 14, 2012 in U.S. Appl. No. 29/376,980.
Office Action dated Jun. 15, 2011 in JP Application No. 2008-538492.
Office Action dated Jun. 15, 2012 in U.S. Appl. No. 29/413,170.
Office Action dated Jun. 21, 2012 in U.S. Appl. No. 12/596,167.
Office Action dated Jun. 8, 2010 in U.S. Appl. No. 12/112,490 by Zinger.
Office Action dated Mar. 1, 2012 in CN Application No. 200880108283.4.
Office Action dated Mar. 10, 2015 in EP Application No. 12 812 395.7.
Office Action dated Mar. 13, 2012 in CA Application No. 2,563,643.
Office Action dated Mar. 17, 2015 in U.S. Appl. No. 14/504,979 by Lev.
Office Action dated Mar. 25, 2016 in U.S. Appl. No. 29/478,726 by Lev.
Office Action dated Mar. 28, 2016 in JP Application No. 2016-507113.
Office Action dated Mar. 6, 2012 in U.S. Appl. No. 12/678,928.
Office Action dated May 12, 2011 in U.S. Appl. No. 12/063,176.
Office Action dated May 27, 2010 in U.S. Appl. No. 11/559,152.
Office Action dated May 28, 2015 in U.S. Appl. No. 14/391,792 by Lev.
Office Action dated May 31, 2013 in U.S. Appl. No. 13/505,790.
Office Action dated May 6, 2014 in U.S. Appl. No. 13/505,881 by Lev.
Office Action dated Nov. 11, 2013 in IL Application No. 218730.
Office Action dated Nov. 28, 2013 in IN Application No. 4348/DELNP/2008.
Office Action dated Nov. 29, 2010 in U.S. Appl. No. 11/568,421.
Office Action dated Oct. 5, 2005 in U.S. Appl. No. 10/062,796.
Office Action dated Oct. 5, 2015 in U.S. Appl. No. 14/385,212 by Lev.
Office Action dated Oct. 6, 2003 in U.S. Appl. No. 10/062,796.
Office Action dated Oct. 8, 2013 in CN Application No. 201080043825.1.
Office Action dated Sep. 28, 2010 in U.S. Appl. No. 12/112,490 by Zinger.
Office Action dated Jul. 31, 2012 in U.S. Appl. No. 12/598,469.
Office Action dated May 25, 2021 issued in Japanese Application No. 2020-553506.
Overview—Silicone Rubber [retrieved from http://www.knovel.com/web/portal/browse/display?EXT_KNOVEL_DISPLAY_bookid=1023&Vertica11D=0 on Feb. 9, 2011].
Photographs of Alaris Medical Systems SmartSite.RTM. device, 5 pages, 2002.
Publication dale of Israeli Patent Application 186290 [on-line]. ]Retrieved from Internet May 24, 2010]. URL:<http://www.ilpatsearch.justrice.gov.il/UI/Requestslistaspx>. (1 page).
Smart Site Needle-Free Systems, Alaris Medical Systems Webpage, 4 pages, Feb. 2006.
Smart Site.RTM. Alaris Medical Systems Product Brochure, 4 pages, Issue 1, Oct. 1999.
Summit International Medical Technologies Inc., Vial Direct to Bag Spike 2020.
The MixJect transfer system, as shown in the article, "Advanced Delivery Devices," Drug Delivery Technology Jul./Aug. 2007 vol. 7 No.7 [on-line]. [Retrieved from Internet May 14, 2010.] URL: <http://www.drugdeiverytech-online.com/drugdelivery/200707/?pg=28pg28>. (3 pages).
Translation of Office Action dated Apr. 15, 2013 in JP Application No. 2008-538492.
Translation of Office Action dated Jun. 18, 2012 in JP Application No. 2008-538492.
U.S. Appl. No. 14/005,751 by Denenburg, filed Sep. 17, 2013.
U.S. Appl. No. 13/505,790 by Lev, filed May 3, 2012.
U.S. Appl. No. 13/505,881 by Lev, filed May 3, 2012.
U.S. Appl. No. 13/522,410 by Lev, filed Jul. 16, 2012.
U.S. Appl. No. 13/576,461 by Lev, filed Aug. 1, 2012.
U.S. Appl. No. 13/883,289 by Lev, filed May 3, 2013.
U.S. Appl. No. 13/884,981 by Denenburg, filed May 13, 2013.
U.S. Appl. No. 14/345,094 by Lev, filed Mar. 14, 2014.
U.S. Appl. No. 14/366,306 by Lev, filed Jun. 18, 2014.
U.S. Appl. No. 14/385,212 by Lev, filed Sep. 15, 2014.
U.S. Appl. No. 14/391,792 by Lev, filed Oct. 10, 2014.
U.S. Appl. No. 14/423,595 by Lev, filed Feb. 24, 2015.
U.S. Appl. No. 14/423,612 by Lev, filed Feb. 24, 2015.
U.S. Appl. No. 14/425,582 by Lev, filed Mar. 3, 2015.
Article with picture of West Pharmaceutical Services' Vial2Bag Needleless System, [on-line]; !Sips Newsletter, Oct. 26, 2007]; retrieved from Internet Feb. 16, 2010]; URL:<http://www.isips.org/reports/ISIPS_Newsletter_October_26_2007. html.> (7 pages. see pp. 5-6).
Decision to Grant dated Apr. 12, 2010 in EP Application No. 08738307.1.
Drug Administration Systems product information sheets; http://www.westpharma.com/eu/en/products/Pages/Vial2Bag.aspx; pp. 1-3 (admitted prior art).
English translation of an Office Action dated Apr. 28, 2014 in JP Application No. 2013-537257.
English translation of an Office Action dated Aug. 28, 2014 in JP Application No. 2013-168885.
English translation of an Office Action dated Dec. 25, 2013 in CN Application No. 201180006530.1.
English translation of an Office Action dated Dec. 4, 2013 in CN Application No. 201080051210.3.
English translation of an Office Action dated Feb. 4, 2014 in JP Application No. 2012-554468.
English translation of an Office Action dated Jan. 9, 2014 in JP Application No. 2010-526421.
English translation of an Office Action dated Jul. 26, 2013 in JP Application No. 2012-538464.
English translation of an Office Action dated Jun. 19, 2013 in JP Application No. 2012-531551.
English translation of an Office Action dated Jun. 30, 2014 in CN Application No. 201180052962.6.
English translation of an Office Action dated Sep. 10, 2013 in JP Application No. 2012-554468.
Extended European Search Report dated Jun. 3, 2014 in EP Application No. 08781828.2.
Facebook "West Pharmaceutical Services, Inc.", first available Oct. 21, 2014 (https://www.facebook.com/westpharma/photos/710246859056351)(2014).
Grifols Vial Adapter Product Literature, 2 pages, Jan. 2002.
http://www.westpharma.com/en/products/Pages/Mixject.aspx (admitted prior art), [Retrieved on Aug. 8, 2012].
http://www.westpharma.com/eu/en/products/Pages/Vial2Bag.aspx; Drug Adminsitration Systems product information sheets pp. 1-3.
Int'l Preliminary Report on Patenability dated Oct. 20, 2009 in Int'l Application No. PCT/IL2008/000517.
Int'l Preliminary Report on Patentability dated Jan. 14, 2014 in Int'l Application No. PCT/IL2012/050516.
Int'l Preliminary Report on Patentability dated May 6, 2008 in Int'l Application No. PCT/IL2006/001228.
Int'l Preliminary Report on Patentability dated May 12, 2014 in Int'l Application No. PCT/IL2013/050316.
Int'l Preliminary Report on Patentability dated Aug. 20, 2014 in Int'l Application No. PCT/IL2012/050407.
Int'l Preliminary Report on Patentability dated Aug. 28, 2012 in Int'l Application No. PCT/IL2011/000186.
Int'l Preliminary Report on Patentability dated Sep. 24, 2013 in Int'l Application No. PCT/IL2012/000354.
Int'l Preliminary Report on Patentability dated Dec. 4, 2007 in Int'l Application No. PCT/IL2006/000912.
Int'l Preliminary Report on Patentability dated Jun. 19, 2006 in Int'l Application No. PCT/IL2005/000376.
Int'l Preliminary Report on Patentability dated Jun. 19, 2008 in Int'l Application No. PCT/IL2007/000343.

(56) References Cited

OTHER PUBLICATIONS

Int'l Search Report & Written Opinion dated Mar. 7, 2012 in Int'l Application No. PCT/IL2011/000829.
Int'l Search Report and Written Opinion dated Mar. 6, 2012 in Int'l Application No. PCT/IL2011/000834.
Int'l Search Report and Written Opinion dated May 8, 2014 in Int'l Application No. PCT/IL2013/050706.
Int'l Search Report and Written Opinion dated Jul. 16, 2014 in Int'l Application No. PCT/IL2014/050327.
Int'l Search Report and Written Opinion dated Sep. 2, 2014 in Int'l Application No. PCT/IL2014/050405.
Int'l Search Report and Written Opinion dated Mar. 23, 2020 in Int'l Application No. PCT/IL2020/050048.
Int'l Search Report dated Feb. 3, 2011 in Int'l Application No. PCT/IL2010/000777; Written Opinion.
Int'l Search Report dated Mar. 17, 2011 in Int'l Application No. PCT/IL2010/000854; Written Opinion.
Int'l Search Report dated Mar. 17, 2011 in Int'l Application No. PCT/IL2010/000915; Written Opinion.
Int'l Search Report dated Mar. 18, 2013 in Int'l Application No. PCT/IL2012/050516.
Int'l Search Report dated Jun. 5, 2013 in Int'l Application No. PCT/IL2012/050407.
Int'l Search Report dated Jun. 19, 2013 in Int'l Application No. PCT/IL2013/050167.
Int'l Search Report dated Jul. 1, 2013 in Int'l Application No. PCT/IL2013/050180.
Int'l Search Report dated Jul. 26, 2013 in Int'l Application No. PCT/IL2013/050316.
Int'l Search Report dated Jul. 31, 2013 in Int'l Application No. PCT/IL2013/050313.
Int'l Search Report dated Aug. 16, 2012 in Int'l Application No. PCT/IL2012/000164.
Int'l Search Report dated Oct. 17, 2005 in Int'l Application No. PCT/IL2005/000376.
Int'l Search Report dated Oct. 17, 2011 in Int'l Application No. PCT/IL2011/000511.
Int'l Search Report dated Nov. 25, 2010 in Int'l Application No. PCT/IL2010/000530.
Int'l Search Report dated Mar. 12, 2009 in Int'l Application No. PCT/IL2008/001278.
Int'l Search Report dated Mar. 27, 2009 in Int'l Application No. PCT/US2008/070024.
Int'l Search Report dated Jul. 12, 2011 in Int'l Application No. PCT/IL2011/000186.
Int'l Search Report dated Jul. 12, 2011 in Int'l Application No. PCT/IL2011/000187.
Int'l Search Report dated Jul. 27, 2007 in Int'l Application No. PCT/IL2007/000343.
Int'l Preliminary Report on Patentability dated Aug. 24, 2015 in Int'l Application No. PCT/IL2014/050405.
Int'l Search Report and Written Opinion dated Jul. 21, 2020 in Int'l Application No. PCT/IL2020/050362.
Int'l Search Report and Written Opinion dated Mar. 29, 2019 in Int'l Application No. PCT/IB2018/059577.
Int'l Search Report and Written Opinion dated May 4, 2011 in Int'l Application No. PCT/IL2010/001077.
Int'l Search Report dated Apr. 24, 2020 in Int'l Application No. PCT/US2020/050020.
Int'l Search Report dated Aug. 25, 2008 in Int'l Application No. PCT/IL2008/000517.
Int'l Search Report dated Jan. 22, 2013 in Int'l Application No. PCT/IL2012/000354.
Int'l Search Report dated Nov. 20, 2006 in Int'l Application No. PCT/IL2006/000881.
International Search Report and Written Opinion dated Oct. 17, 2014 in International Application No. PCT/IL2014/050680.
International Search Report dated Jan. 23, 2007 in Int'l Application No. PCT/IL/2006/001228.
International Search Report dated Mar. 30, 2011 in Int'l Application No. PCT/IL2010/000939.
International Search Report dated Aug. 28, 2008 in Int'l Application No. PCT/IL2008/000606.
Intl Search Report dated Dec. 6, 2006 in Int'l Application No. PCT/IL2006/000912.
IV disposables sets catalogue, Cardinal Health, Alaris(Registered) products, SmartSite(Registered) access devices and accessories product No. 10013365, SmartSite add-0n bag access device with spike adapter and needle-free valve bag access port, pp. 1-5, Fall edition (2007).
Merchant "An engineered control device for needle free reconstitution and transfer of compounded sterile intravenous Drug solutions for immediate use to assist in complying with United States Pharmacopeia Chapter <797> standard", Adv Care, 2 pages, 2018.
MixJect, downloaded from webpage: http://www.westpharma.com/en/products/Pages/MixjecI.aspx, Download Date: Aug. 8, 2012, 1 page.
MixJet Product Information Sheet, downloaded from webpage: http://www.westpharma.com/SiteCollectionDocuments/Recon/mixject%20product%20sheet.pdf; 1 page.
Non-Vented Vial Access Pin with ULTRASITE.RM. Valve, B. Braun Medical, Inc. website and product description, 3 pages, Feb. 2006.
Notice of Allowance dated Jan. 12, 2016 in U.S. Appl. No. 14/385,212 by Lev.
Notice of Allowance dated Mar. 17, 2016 in U.S. Appl. No. 29/502,037 by Lev.
Novel Transfer, Mixing and Drug Delivery System, MOP Medimop Medical Projects Ltd. Catalog, 4 pages, Rev. 4, 2004.
Office Action dated Apr. 17, 2014 in CN Application No. 201080051201.4.
Office Action dated Apr. 2, 2013 in U.S. Appl. No. 13/505,790.
Office Action dated Apr. 20, 2010 in U.S. Appl. No. 11/997,569.
Office Action dated Apr. 9, 2015 in U.S. Appl. No. 13/883,289 by Lev.
Office Action dated Aug. 20, 2013 in U.S. Appl. No. 13/576,461 by Lev.
Office Action dated Aug. 24, 2015 in U.S. Appl. No. 14/366,306 by Lev.
Office Action dated Aug. 3, 2011 in JP Application No. 2008-525719.
Office Action dated Aug. 7, 2015 in JP Application No. 2015-529206.
Office Action dated Dec. 13, 2010 in U.S. Appl. No. 12/293,122.
Office Action dated Dec. 20, 2010 in U.S. Appl. No. 12/063,176.
Office Action dated Dec. 23, 2010 in U.S. Appl. No. 29/334,696.
Office Action dated Dec. 9, 2015 in U.S. Appl. No. 29/478,723 by Lev.
Office Action dated Dec. 9, 2015 in U.S. Appl. No. 29/478,726 by Lev.
Office Action dated Feb. 13, 2014 in U.S. Appl. No. 13/884,981 by Denenburg.
Office Action dated Feb. 20, 2009 in U.S. Appl. No. 11/694,297.
Office Action dated Feb. 22, 2005 in U.S. Appl. No. 10/062,796.
Office Action dated Feb. 7, 2011 in U.S. Appl. No. 12/783,194.
Office Action dated Jan. 17, 2014 in CN Application No. 201180006534.X.
Office Action dated Jan. 2, 2014 in U.S. Appl. No. 13/505,881 by Lev.
Office Action dated Jan. 2, 2015 in U.S. Appl. No. 29/438,141 by Gilboa.
Office Action dated Jan. 20, 2010 in JP Application No. 2007-510229.
Office Action dated Jan. 23, 2013 in U.S. Appl. No. 12/112,490 by Zinger.
Office Action dated Jan. 5, 2015 in U.S. Appl. No. 29/413,220 by Lev.
Office Action dated Jul. 11, 2011 in U.S. Appl. No. 12/293,122.
Office Action dated Jul. 13, 2012 in U.S. Appl. No. 12/112,490 by Zinger.

(56) References Cited

OTHER PUBLICATIONS

Office Action dated Jul. 31, 2014 in U.S. Appl. No. 29/438,141 by Gilboa.
Office Action dated Jun. 1, 2010 in U.S. Appl. No. 11/568,421.

* cited by examiner

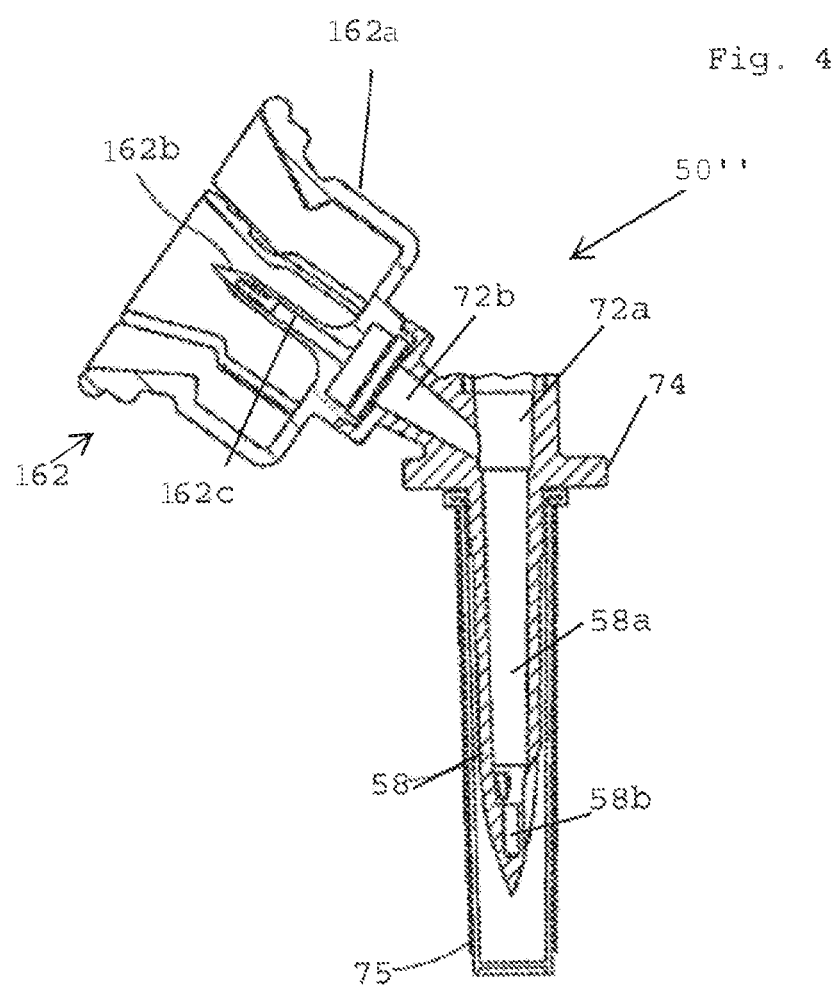

LIQUID TRANSFER DEVICE

CROSS-REFERENCE TO RELATED APPLICATIONS

This application is a section 371 of International Application No. PCT/IB2020/050790, filed Jan. 31, 2020, which was published on Aug. 6, 2020 under International Publication No. WO 2020/157719 A1, which claims the benefit of U.S. Provisional Application No. 62/799,317, filed Jan. 31, 2019, the disclosures of which are incorporated herein by reference.

BACKGROUND OF THE INVENTION

The invention relates to liquid transfer devices.

Conventional infusion liquid containers containing an infusion liquid to be delivered to a patient generally take the form of an infusion liquid bag, an infusion liquid bottle, and the like. A pre-filled syringe or vial is generally utilized to add a liquid drug to the infusion liquid contents, via a liquid transfer device, to form a medicated infusion liquid. Thereafter, an infusion set including an IV spike is generally inserted into an IV port of the liquid transfer device for infusion of medicated infusion liquid contents to a patient.

Typically, the IV port is connected to the remainder of the liquid transfer device via an adhesive bond. A covering, twist-off member, requiring the application of torque for removal, must be removed to access the IV port. How a user grips the liquid transfer device to remove the twist-off member may result in exposing the adhesive bond to the torque. Damage to the adhesive bond compromises the liquid transfer device.

Accordingly, it would be advantageous to manufacture a liquid transfer device having a rotationally fixed mechanical connection between the IV port and the remainder of the liquid transfer device, engineered to withstand such torque without causing damage thereto.

BRIEF DESCRIPTION OF THE DRAWINGS

The following description of embodiments of the invention will be better understood when read in conjunction with the appended drawings. It should be understood, however, that the invention is not limited to the precise arrangements and instrumentalities shown. In the drawings:

FIG. 4 is a partial, cross-sectional elevation view of a third configuration of the liquid transfer device according to the present invention, taken along a sectional line such as line 2*b*-2*b* of FIG. 2A.

DESCRIPTION OF THE INVENTION

Figure 1A:
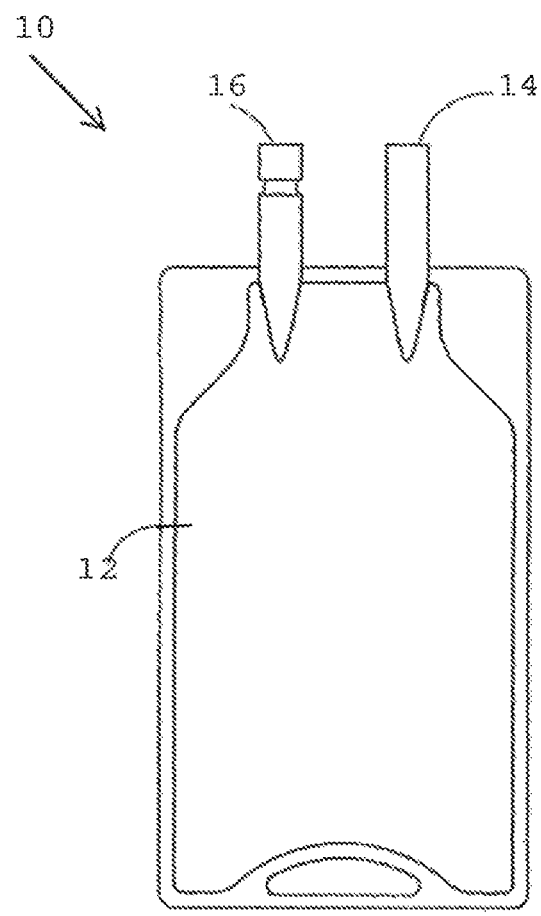
FIG. 1A is a front elevational view of an infusion bag usable with a liquid transfer device according to the present invention.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the liquid transfer device, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 1B:
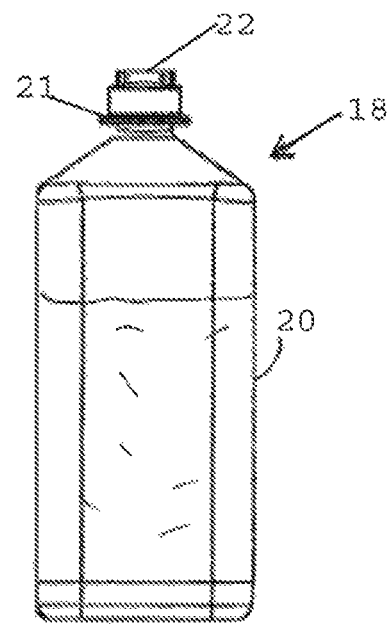
FIG. 1B is a front elevational view of an IV bottle usable with a liquid transfer device according to the present invention.
Figure 1C:
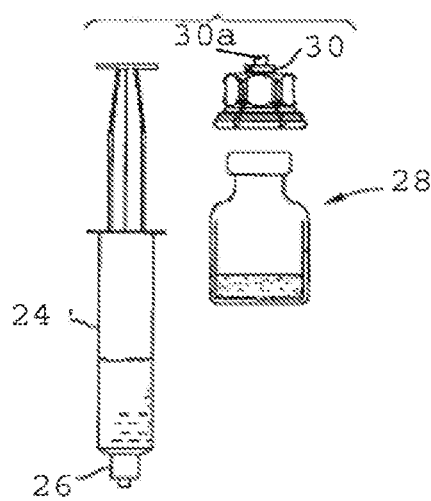
FIG. 1C is a front elevational view of a pre-filled needleless syringe, a male vial adapter, and vial usable with the liquid transfer device according to the present invention.

Referring to the drawings in detail, wherein like numerals indicate like elements throughout, there is shown in FIGS. 2A-4, multiple configurations of a liquid transfer device 50, 50', 50" intended for use with infusion liquid containers containing an infusion liquid and with additive transfer devices. Such infusion liquid containers may take the form of an infusion liquid bag 10 (FIG. 1A), an infusion liquid bottle 18 (FIG. 1B) and the like, and such additive transfer devices may take the form of a syringe 24 (FIG. 1C) having a male connector 26, e.g., a male luer connector, a sealed vial 28 (FIG. 1C) connectable to a vial adapter 30 or 62 (as will be further explained below), and the like.

As should be understood by those of ordinary skill in the art, a conventional infusion liquid bag 10 (FIG. 1A) includes a reservoir 12 containing infusion liquid, in fluid communication with an intravenous (IV) or administration port 14 and an additive port 16. The infusion liquid bag 10 is collapsible upon administration of the infusion liquid therefrom. A conventional infusion liquid bottle 18 (FIG. 1B) also includes a reservoir 20 containing infusion liquid and is sealingly closed by a stopper 22 (in a manner well understood by those of ordinary skill in the art). The infusion liquid bottle 18 may be constructed from a collapsible material intended to collapse upon administration of the infusion liquid therefrom, or, alternatively, from a non-collapsible material, e.g., a polymeric or plastic material (hereinafter referred to as "plastic"), glass, and the like.

A syringe 24 is generally pre-filled with a medicament liquid for injection either into the infusion liquid bag 10 or bottle 18 for mixing with the infusion liquid therein to form a medicated infusion liquid for administration to a patient or direct administration to a patient. Similarly, a vial 28 generally contains a medicament liquid additive or a lyophilized powder drug requiring reconstitution prior to administration. The contents of the vial 28 are introduced into the infusion liquid bag 10 or bottle 18 for mixing with the infusion liquid to form a medicated infusion liquid for administration to a patient (as will be described in further detail below).

Turning to FIGS. 2A-4, the liquid transfer device 50, 50', 50" includes a trifurcated connector body 52. The trifurcated connector body 52 includes an IV port 54 at a first end thereof (FIGS. 2A-4). In one configuration, as shown in FIGS. 2A-2D, the trifurcated connector body 52 includes a vial adapter 56 at a second end thereof. Alternatively, in another configuration, as shown in FIGS. 3A and 4, the trifurcated connector body 52 may include an IV spike 58 at the second end thereof. In one configuration, as shown in FIGS. 2A, 2B, 2D and 3A-3D, the trifurcated connector body 52 further includes a normally closed (NC) needleless additive port 60 at a third end thereof. Alternatively, in another configuration, as shown in FIG. 4, the trifurcated connector body 52 may include a vial adapter 162 at the third end thereof. That is, in exemplary configurations, the liquid transfer device 50 may include an IV port 54 at the first end thereof, a vial adapter 56 or an IV spike 58 at the second end thereof, and a needleless additive port 60 or a vial adapter 162 at the third end thereof, but the disclosure is not so limited.

Turning to FIGS. 2A-2D, the trifurcated connector body 52 may include the vial adapter 56 at the second end thereof for using the liquid transfer device 50 with liquid infusion bottles 18. The vial adapter 56 is constructed from a suitable rigid plastic material, such as, for example, polycarbonate and the like. The vial adapter 56 includes a transversely extending top surface 64 at the second end of the connector body 52 and a skirt 66 downwardly depending from the top surface 64, configured, e.g., sized and dimensioned, for telescopically snap fit mounting onto an IV bottle 18 (in a manner well understood by those of ordinary skill in the art). A puncturing cannula 68, having a liquid lumen 69 with peripherally disposed apertures 69a proximate a spiked end thereof, projects downwardly from the transverse vial adapter top surface 64 for puncturing the IV bottle stopper 22 upon telescopically snap fit mounting the vial adapter 56 on an IV bottle 18. The vial adapter skirt 66 includes at least two inwardly directed protrusions 70 (FIG. 2C) for snap fitting under a flange 21 of the IV bottle 18 underlying the stopper 22. In one embodiment, the puncturing cannula 68 may have an approximately 3 mm external diameter.

The connector body 52 defines a lumen 72 in continuous fluid communication with the lumen 69 of the puncturing cannula 68 of vial adapter 56 and projecting from the top surface 64 of the vial adapter 56 in an opposite direction from the puncturing cannula 68. The lumen 72 bifurcates into a first lumen 72a (within a nipple portion 88) and a second lumen 72b. In the illustrated embodiment, the first lumen 72a is co-directional with the lumen 69, but the disclosure is not so limited. The second lumen 72b is angled relative to, i.e., branches off of, the first lumen 72a and the lumen 69. As shown best in FIGS. 2B, 2C, the first lumen 72a may include an inline particulate filter 73 to prevent communication of solid particulate between the lumen 69 and the lumens 72a, 72b.

Figure 3A:
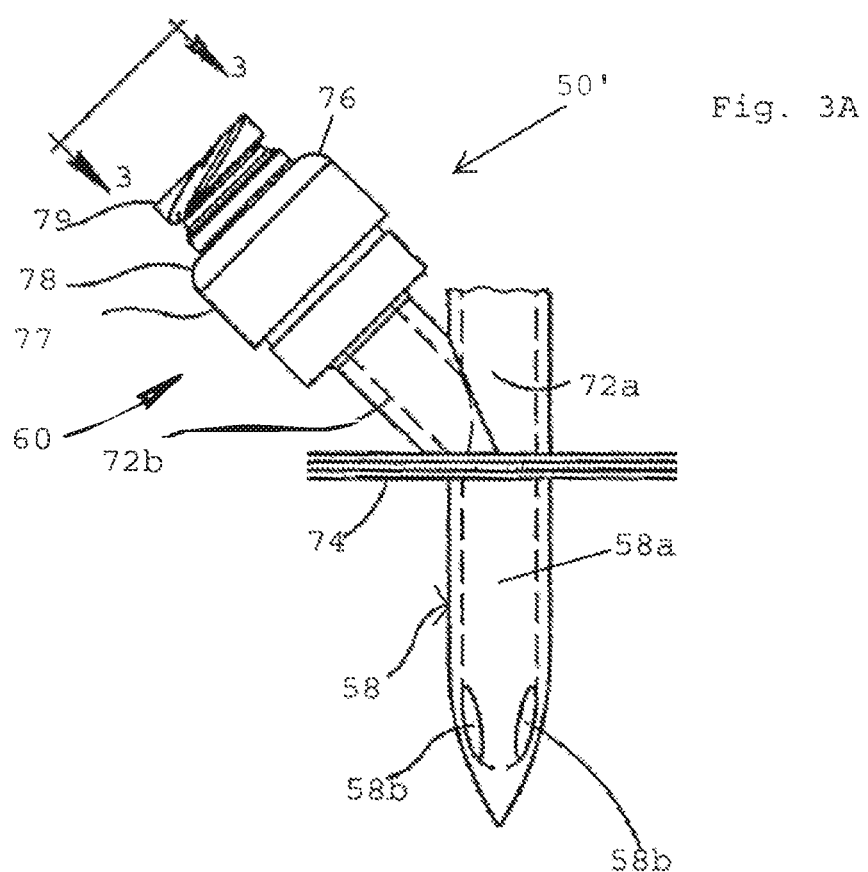
FIG. 3A is a partial, front elevational view of a second configuration of the liquid transfer device according to the present invention.

As shown in FIGS. 3A and 4, another configuration of the trifurcated connector body 52 of liquid transfer devices 50', 50" includes the IV spike 58 at the second end thereof for using the liquid transfer device 50 with infusion liquid bags 10, i.e., for sealingly inserting the IV spike 58 into the IV port 14 of the bag 10. The IV spike 58 is also constructed from a suitable rigid plastic material, such as, for example, polycarbonate and the like. The IV spike 58 includes an internal liquid lumen 58a (co-directional with the lumen 72a and in continuous fluid communication with both lumens 72a, 72b) with peripherally disposed apertures 58b proximate the spike end thereof. A flange 74 extends laterally from the IV spike 58 proximate an opposing end thereof, for restricting insertion depth into the IV port 14 of the bag 10. In one embodiment, the IV spike 58 is integrally formed as an injection molded monolithic structure with the flange 74, but the disclosure is not so limited. A spike cap 75 (FIG. 4) may removably cover the spike 58 when not in use.

Figure 2A:
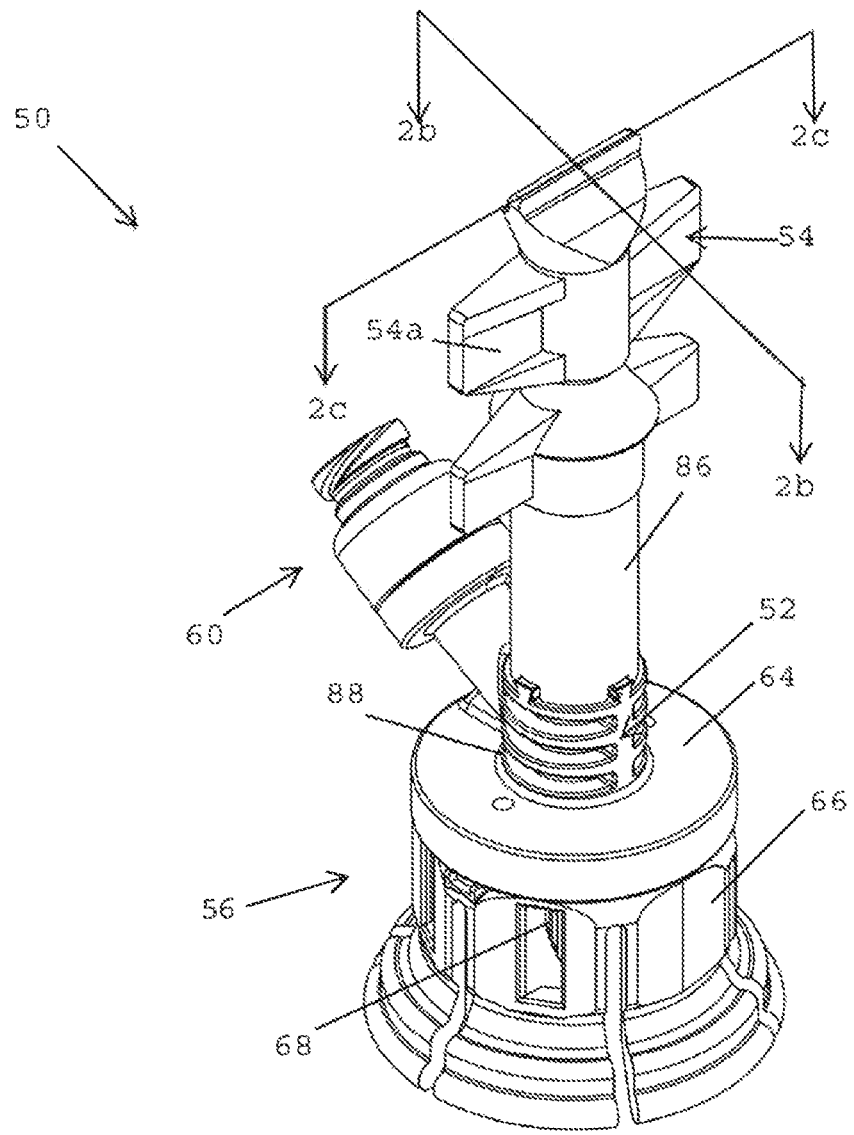
FIG. 2A is a perspective view of a first configuration of the liquid transfer device according to the present invention.
Figure 2B:
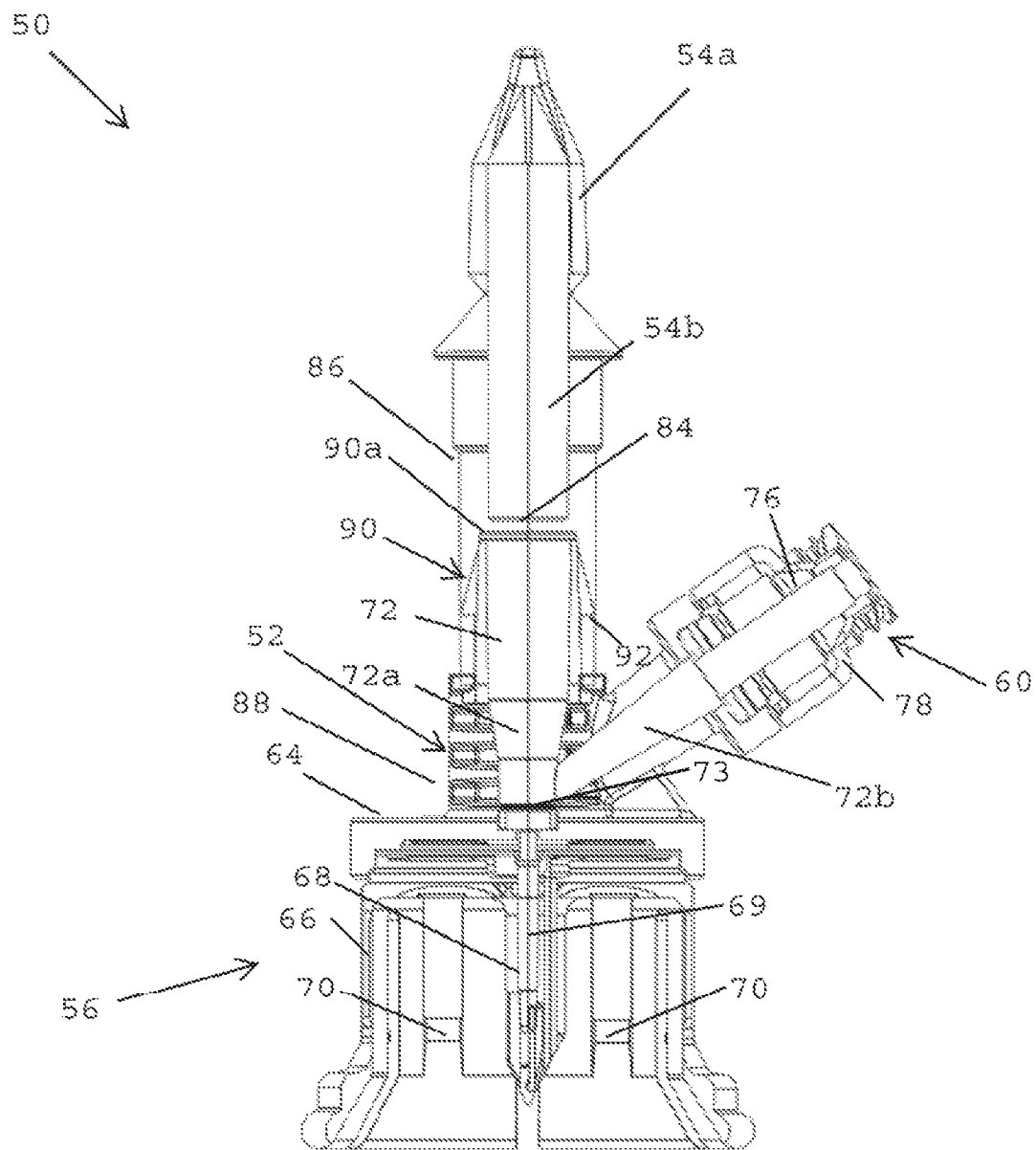
FIG. 2B is a cross-sectional elevational view of the liquid transfer device of FIG. 2A, taken along sectional line 2*b*-2*b* of FIG. 2A.
Figure 2C:
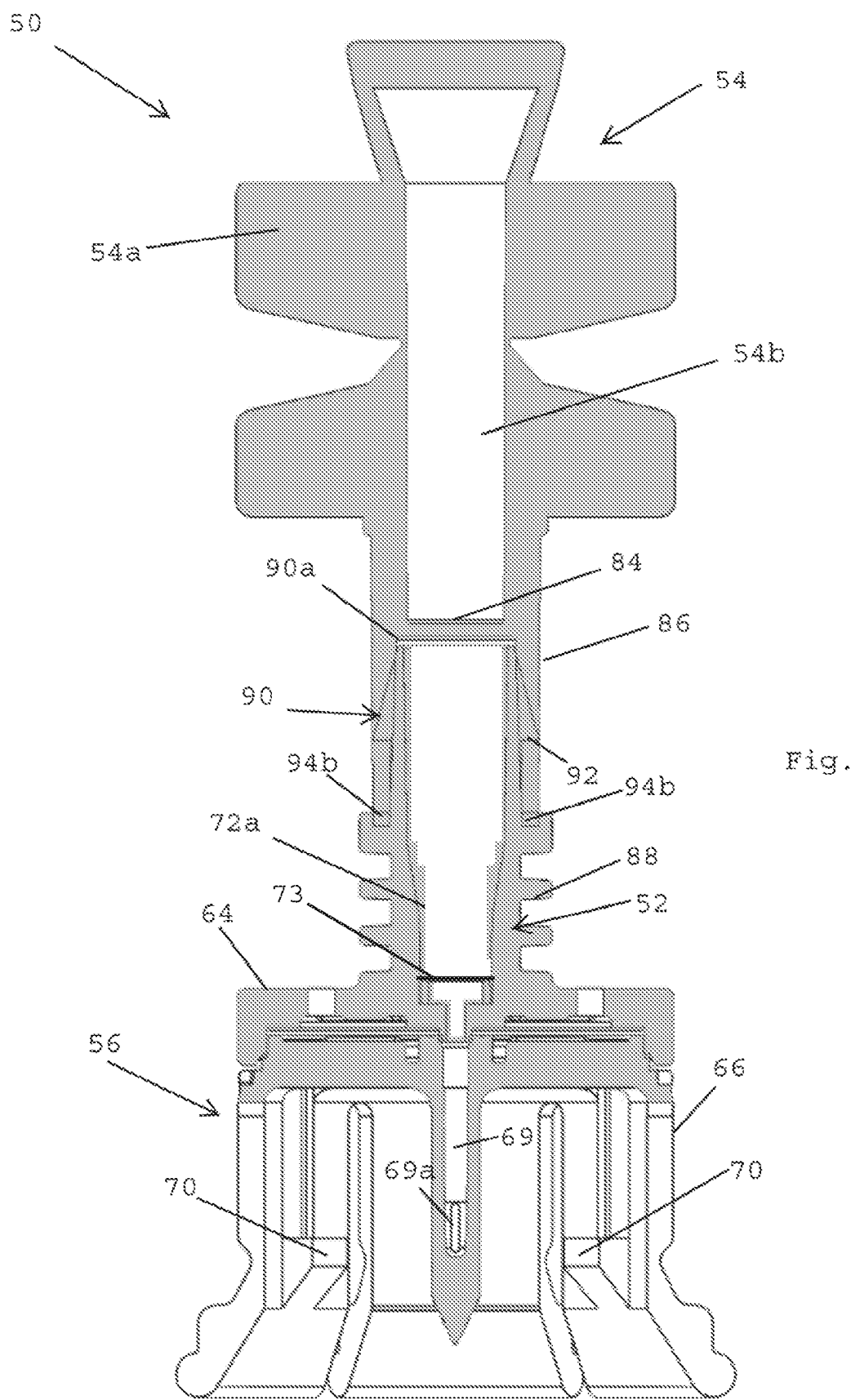
FIG. 2C is a cross-sectional elevational view of the liquid transfer device of FIG. 2A, taken along sectional line 2*c*-2*c* of FIG. 2A.
Figure 2D:
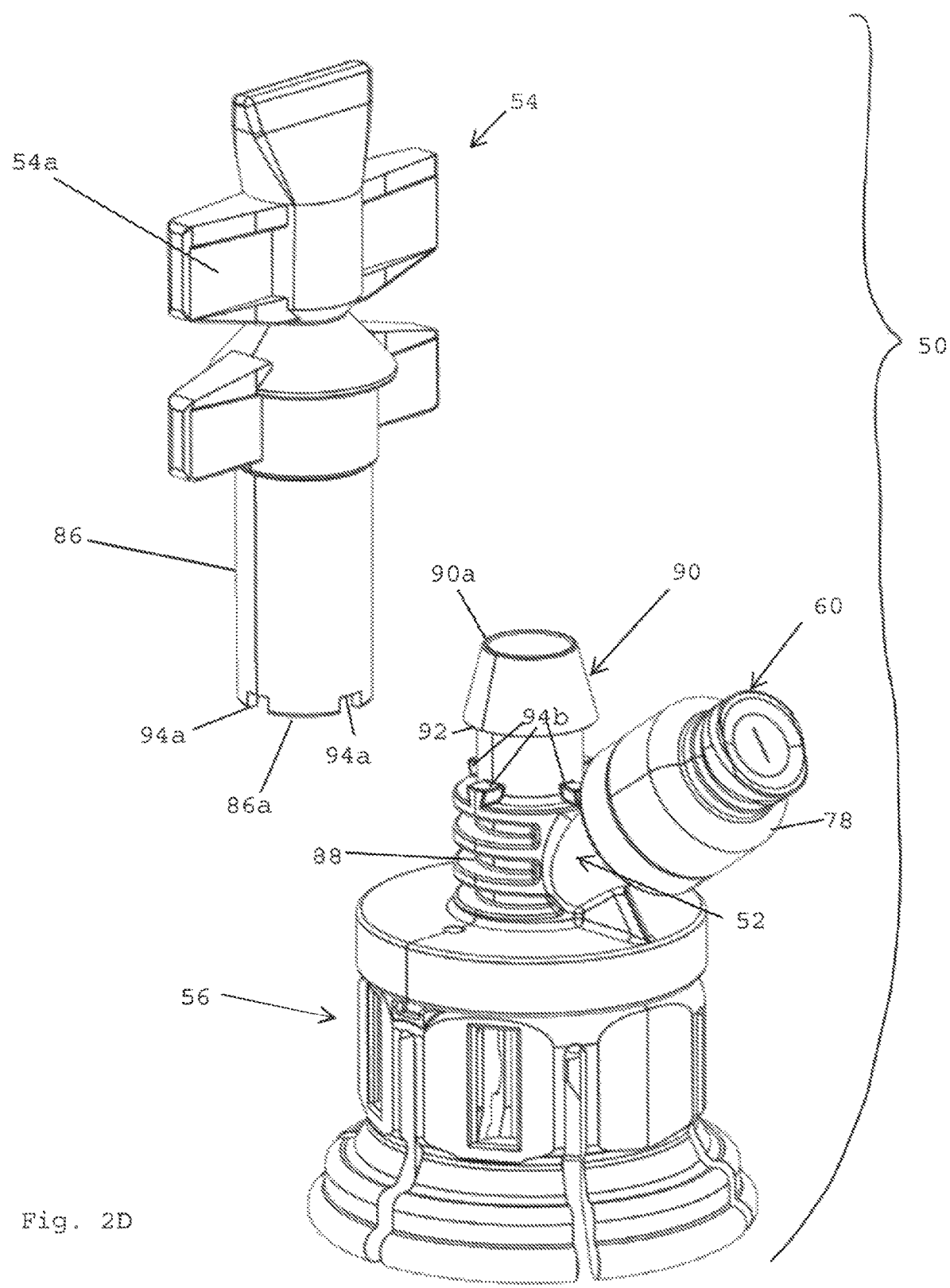
FIG. 2D is an exploded, perspective view of the liquid transfer device of FIG. 2A.
Figure 3B:
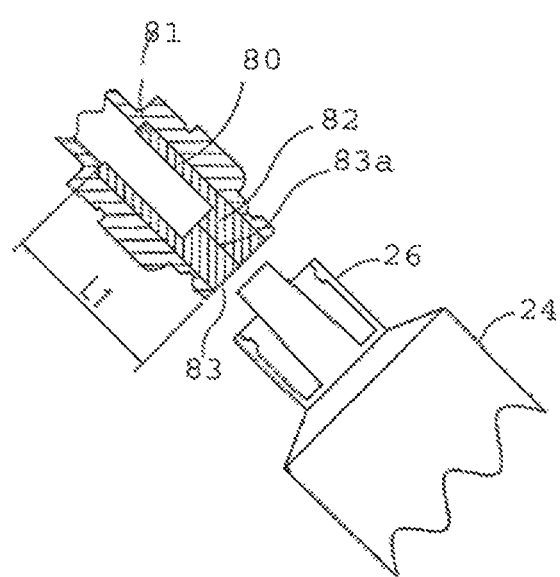
FIG. 3B is an expanded cross-sectional elevational view of a self-sealing access valve of the liquid transfer device of FIG. 3A, in a closed position thereof, taken along sectional line 3-3 of FIG. 3A.
Figure 3C:
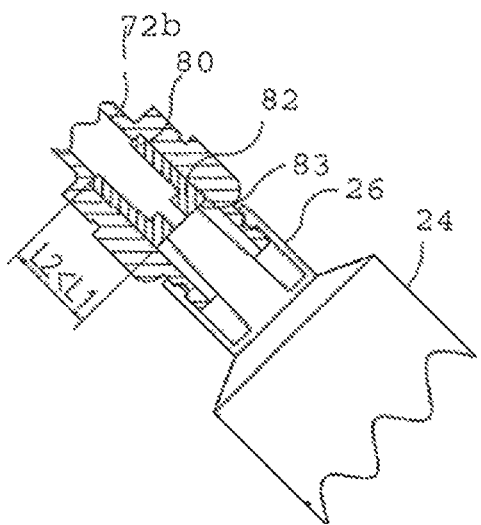
FIG. 3C is an expanded cross-sectional elevational view of the self-sealing access valve, in an open position thereof, taken along sectional line 3-3 of FIG. 3A.
Figure 3D:
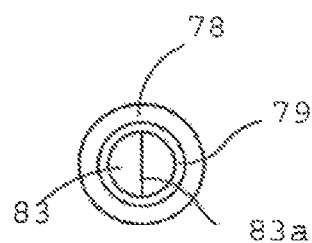
FIG. 3D is a top plan view of the self-sealing access valve.

As shown in FIGS. 2A-3D, the trifurcated connector body 52 may include the needleless additive port 60 integrally formed at the third end thereof, for using the liquid transfer device 50 with any additive transfer device having a male connector, e.g., a syringe 24 or a vial 28 mounted to a vial adapter 30. The needleless additive port 60 is positioned at the peripheral end of the second lumen 72b, and is fitted with a self-sealing access valve 76 for screw threadingly receiving a male connector. The access valve 76 is typically constructed from a rigid transparent plastic material such as, for example, polycarbonate and the like. The access valve 76 has a stepped exterior surface 77 including an abutment surface 78 and a rim 79. The access valve 76 houses a silicone self-sealing valve member 80 (FIGS. 3B, 3C) with a tubular main portion 81 and a cylindrical needleless entry portion 82. The needleless entry portion 82 has an exposed entry surface 83 and a pre-formed slit 83a extending therealong (FIGS. 3B-3D). The self-sealing valve member 80 has a natural length L1 and is so dimensioned that the entry surface 83 is flush with the rim 79 thereby enabling the entry surface 83 to be readily swabbed for sterilization purposes (see FIG. 3B).

As shown best in FIGS. 3B and 3C, a male connector, e.g., the mail luer connector 26 of the syringe 24, may be screw threaded onto the needle additive port 60 and advanced until the connector 26 abuts against the abutment surface 78. During advancement, the male Luer connector 26 compresses the valve member 80 to a compressed length L2<L1 which parts the entry surface 83 along its pre-formed slit 83a for enabling fluid communication between the syringe 24 and the lumen 72b (see FIG. 3C). As should be understood by those of ordinary skill in the art, a syringe 24 can be pre-filled with a liquid additive. Alternatively, a syringe 24 can be filled with a liquid drug reconstituted from a lyophilized powder drug vial. A reconstituted liquid drug may have been reconstituted with liquid contents aspirated from an infusion bag 10, an infusion liquid bottle 18 and the like. As also should be understood, a male luer connector 30a of a vial adapter 30 may be screw threaded onto the needleless additive port 60 in the same manner. The vial adapter 30 is snap fit telescopically mountable onto a vial 28 in a manner well understood by those of ordinary skill in the art to enable usage of the device 50 with an additive transfer device in the form of a vial 28. The vial 28 may contain a liquid additive mixable with an infusion liquid prior to administration of infusion liquid to a patient or administered to a patient during an infusion procedure. In the case that the vial 28 contains a lyophilized powder drug, the drug can be reconstituted by squeezing on the infusion bag 10 or an infusion bottle 18 for forcing liquid from the infusion bag 10 or bottle 18 into the vial 28. Thus, as should be understood by those of ordinary skill in the art, upon coupling of the liquid transfer device 50 on a infusion liquid bag 10 or an infusion liquid bottle 18 (as previously explained), and coupling of the liquid transfer device 50 with a syringe 24 or a vial 28 (as previously explained), the contents within the liquid bag 10 or an infusion liquid bottle 18 are fluidly connected and mixable/combinable with the contents within the syringe 24 or a vial 28, via the fluidly connected lumens 72a, 72b of the connector body 52.

Alternatively, the liquid transfer device 50 may be dedicated for use with an additive transfer device in the form of the vial 28. That is, in an alternative configuration, and as shown in FIG. 4, the vial adapter 162 of the liquid transfer device 50" may be integrally formed at the third end of the trifurcated connector body 52. The integral vial adapter 162 includes a skirt 162a for telescopic snap fit mounting onto a vial 28 (in the standard manner) and a cannula 162b for puncturing the vial 28, e.g., via a stopper thereof, for fluid communication therewith. The puncturing cannula 162b includes a lumen 162c in fluid communication with the second lumen 72b, and, in turn with the first lumen 72a. Adding/mixing of the contents within the vial 28 may be performed as previously explained.

Irrespective of the liquid transfer device 50 configurations with respect to the second or third ends of the trifurcated connector body 52, the body 52 includes the IV port 54 at the first end thereof. As shown in FIGS. 2A-2D, the IV port 54 includes a twist-off member 54a proximate a peripheral, free end of the port 54, and an elongate connecting member 86 projecting therefrom, having an internal lumen 54b extending therethrough and terminating in an open end 86a (opposite the twist-off member 54a). The internal lumen 54b of the assembled liquid transfer device 50 extends co-directionally with the first lumen 72a of the trifurcated connector body 52. In one embodiment, the IV port 54 may be constructed from a suitable flexible plastic material, such as, for example, PVC, and the like.

The IV port 54 includes a sealing membrane 84 generally transversely positioned within the elongate connecting member 86 (see FIGS. 2B, 2C), extending across the internal lumen 54b. Accordingly, the twist-off member 54a may be removed without leading to flow communication beyond the sealing membrane 84. Flow communication beyond the sealing membrane 84 is only achieved upon puncturing the sealing membrane 84 (as discussed in further detail below). Thus, the twist off member 54a keeps the sealing membrane 84 sterile until use.

As shown best in FIGS. 2A-2D, the connector body 52 includes the nipple portion 88 projecting upwardly from the transverse vial adapter top surface 64 (or from the IV spike 58—not shown), i.e., away from the vial adapter 56 or IV spike 58, and defining the first lumen 72a therein. The nipple portion 88 terminates in a barbed fitting member 90 having an open end 90a, such that the first lumen 72a (and, therefore, the second lumen 72b) is in fluid communication with the internal lumen 54b of the elongate connecting member 86. The barbed fitting member 90 is configured, i.e., size, dimension, material, relative to the internal diameter and material of the elongate connecting member 86 to advance into the internal lumen 54b through the open end 86a, and form a barbed, friction, i.e., interference, fit therebetween. As should be understood by those of ordinary skill in the art, the barbed fitting member 90 permits advancement thereof into the internal lumen 54b to sealingly and securely mount the IV port 54 co-directionally upon the nipple portion 88 of the connector body 52, and also substantially prevent withdrawal of the nipple portion 88 without damaging at least one of the elongate connecting member 86 and the barbed fitting member 90.

That is, and as shown, the barbed fitting member 90 is frustoconically shaped, having a progressively increasing diameter in a direction away from the open end 90a. An opposing end of the barbed fitting member 90 defines a greater diameter from the underlying nipple portion 88, resulting in an annular rib 92 that bites into the interior sidewall of the elongate connecting member 86, upon attempted withdrawal of the barbed fitting member 90 out of the elongate connecting member 86. Accordingly, the barbed fitting member 90 is advanceable into the internal lumen 54b of the elongate connecting member 86 during assembly, and, thereafter, is not readily able to be withdrawn without causing damage.

As shown best in FIG. 2D, the rim of the elongate connecting member 86 defining the open end 86a thereof includes at least one cutout 94a, and the nipple portion 88 includes a corresponding at least one radial tab 94b configured to mate therewith. In the illustrated embodiment, the elongate connecting member 86 includes a plurality of angularly spaced cutouts 94a, and the nipple portion 88 includes a corresponding plurality of angularly spaced tabs 94b. The tab(s) 94b mates with the cutout(s) 94a during mounting of the IV port 54 upon the barbed fitting member 90 of the connector body 52, to rotationally fix the IV port 54 relative to the remainder of the liquid transfer device 50. Advantageously, therefore, the IV port 54 is both sealingly assembled with the connector body 52 in a mechanical manner, as well as sufficiently rotationally fixed with the connector body 52 in a mechanical manner, to minimize damage to the connection therebetween during the application of torque upon twisting off the twist-off member 54a.

Figure 1D:
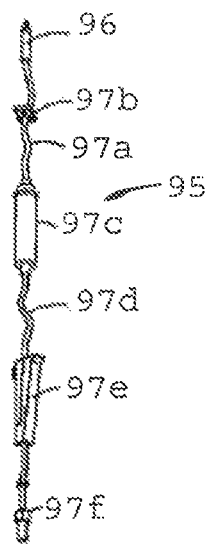
FIG. 1D is a front elevational view of a of an infusion set usable with the liquid transfer device according to the present invention.

In use, after coupling of the liquid transfer device 50 on a infusion liquid bag 10 or an infusion liquid bottle 18 (as previously explained), coupling of the liquid transfer device 50 with a syringe 24 or a vial 28 (as previously explained), and mixing and/or adding the contents within the liquid bag 10 or an infusion liquid bottle 18 with the contents within the syringe 24 or a vial 28 (to create a medicated infusion liquid), the twist-off member 54a is removed, providing access to the internal lumen 54b. Thereafter, an IV spike 96 of an infusion set 95 (FIG. 1D) is sealingly inserted into the internal lumen 54b and penetrates the sealing membrane 84, thereby fluidly connecting the IV spike 96 with any remainder of the internal lumen 54b beyond the sealing membrane 84, and, in turn, with the first and second lumens 72a, 72b for administration of the medicated infusion liquid to a patient. Conventionally, an infusion set 50 additionally includes first tubing 97a, a clamp 97b, a drip chamber 97c, second tubing 97d, a roller clamp 97e, and a male Luer connector 97f for controlling fluid administration to a patient.

As best shown in FIG. 2D, each of the cutouts 94a can be equidistantly radially spaced apart. Likewise, each of the tabs 94b can be equidistantly radially spaced apart. However, other spacings for the cutouts 94a and the tabs 94b are contemplated. Further, each of the tabs 94b can have a rectangular cross-section, and the cutouts 94a can define a shape complementary to the tabs 94b. However, other shapes for the cutouts 94a and the tabs 94a are contemplated.

It will be appreciated by those skilled in the art that changes could be made to the embodiments described above without departing from the broad inventive concepts thereof. As one non-limiting example, the needleless additive port 60 can be replaced by a manually operated stop cock, and the like. It is understood, therefore, that this invention is not limited to the particular embodiments disclosed, but it is intended to cover modifications within the spirit and scope of the present invention.

The invention claimed is:

1. A liquid transfer device comprising:
a connector body comprising a projection portion defining at least one tab; and
an intravenous (IV) port comprising an elongate connecting member and a twist-off member, the IV port being arranged at a first end of the connector body, the elongate connecting member projecting therefrom and defining at least one cutout, and the twist-off member being arranged to provide access to the IV port once removed with an application of torque,
wherein the projection portion is configured to be received by the elongate connecting member, and the at least one tab is configured to mate with the at least one cutout so as to rotationally fix the IV port relative to the connector body.

2. The liquid transfer device of claim 1, wherein the at least one cutout includes a plurality of cutouts that are angularly spaced apart, and the at least one tab includes a plurality of tabs that are angularly spaced apart.

3. The liquid transfer device of claim 2, wherein each of the plurality of tabs has a substantially rectangular cross-section.

4. The liquid transfer device of claim 1, wherein the twist-off member comprises a breakable section configured to break upon the application of torque to the twist-off member.

5. The liquid transfer device of claim 1, wherein the connector body is a trifurcated connector body.

6. The liquid transfer device of claim 1, further comprising a vial adapter or an IV spike at a second end of the connector body.

7. The liquid transfer device of claim 6, further comprising a needleless additive port or a vial adapter at a third end of the connector body.

8. The liquid transfer device of claim 1, wherein the projection portion comprises a fitting member for sealingly mounting the IV port to the projection portion.

9. The liquid transfer device of claim 8, wherein the fitting member comprises an open end and is frustoconically shaped having a progressively increasing diameter in a direction away from the open end.

10. The liquid transfer device of claim 8, wherein the fitting member has a barbed shape with an annular rib configured to substantially prevent withdrawal of the projection portion from the IV port without damaging at least one of the IV port and the projection portion.

11. A liquid transfer device comprising:
a connector body comprising a projection portion defining at least one tab;
an IV port arranged at a first end of the connector body, the IV port comprising an elongate connecting member projecting therefrom and defining at least one cutout;
a vial adapter configured for mounting on an IV bottle and arranged at a second end of the connector body; and
an additive port arranged at a third end of the connector body,
wherein the projection portion is configured to be received by the elongate connecting member, and the at least one tab is configured to mate with the at least one cutout so as to rotationally fix the IV port relative to the connector body, and
wherein the connector body provides fluid communication between the IV port, the vial adapter, and the additive port.

12. The liquid transfer device of claim 11, wherein the vial adapter comprises a puncturing cannula for puncturing an IV bottle stopper.

13. The liquid transfer device of claim 11, wherein the connector body defines a lumen in continuous fluid communication with a lumen of a puncturing cannula of the vial adapter, and the lumen bifurcates into a first lumen within the projection portion and a second lumen, the additive port being positioned at a peripheral end of the second lumen.

14. The liquid transfer device of claim 11, wherein the additive port includes a self-sealing valve.

15. The liquid transfer device of claim 11, wherein the at least one cutout includes a plurality of cutouts that are angularly spaced apart, and the at least one tab includes a plurality of tabs that are angularly spaced apart.

16. The liquid transfer device of claim 15, wherein each of the plurality of tabs has a substantially rectangular cross-section.

17. A liquid transfer device comprising:
a connector body comprising a projection portion defining at least one tab;
an IV port arranged at a first end of the connector body, the IV port comprising an elongate connecting member projecting therefrom and defining at least one cutout;
an IV spike arranged at a second end of the connector body; and
an additive port arranged at a third end of the connector body,
wherein the projection portion is configured to be received by the elongate connecting member, and the at least one tab is configured to mate with the at least one cutout so as to rotationally fix the IV port relative to the connector body, and
wherein the connector body provides fluid communication between the IV port, the IV spike, and the additive port.

18. The liquid transfer device of claim 17, wherein the connector body defines a lumen in continuous fluid communication with a lumen of a puncturing cannula of the IV spike, and the lumen bifurcates into a first lumen within the projection portion and a second lumen, the additive port being positioned at a peripheral end of the second lumen.

19. The liquid transfer device of claim 17, wherein the at least one cutout includes a plurality of cutouts that are angularly spaced apart, and the at least one tab includes a plurality of tabs that are angularly spaced apart.

20. The liquid transfer device of claim 19, wherein each of the plurality of tabs has a substantially rectangular cross-section.

* * * * *